(12) United States Patent
Greenberg et al.

(10) Patent No.: US 9,199,026 B2
(45) Date of Patent: Dec. 1, 2015

(54) MODULAR EXTRACORPOREAL SYSTEMS AND METHODS FOR TREATING BLOOD-BORNE DISEASES

(75) Inventors: David G. Greenberg, Phoenix, AZ (US); Scott Puritz, Chevy Chase, MD (US); Tatiana Koutchma, Countryside, IL (US); Juan N. Walterspiel, Belmont, CA (US)

(73) Assignee: SOMERSET GROUP ENTERPRISES, INC., Bethesda, MD (US)

( * ) Notice: Subject to any disclaimer, the term of this patent is extended or adjusted under 35 U.S.C. 154(b) by 0 days.

(21) Appl. No.: 13/346,321

(22) Filed: Jan. 9, 2012

(65) Prior Publication Data

US 2012/0189711 A1    Jul. 26, 2012

Related U.S. Application Data

(60) Provisional application No. 61/430,634, filed on Jan. 7, 2011.

(51) Int. Cl.
*A61M 1/14* (2006.01)
*A61M 1/16* (2006.01)
(Continued)

(52) U.S. Cl.
CPC .................. *A61M 1/36* (2013.01); *A61K 35/14* (2013.01); *A61M 1/14* (2013.01); *A61M 1/16* (2013.01);
(Continued)

(58) Field of Classification Search
CPC ....... A61M 1/1698; A61M 1/16; A61M 1/36; A61M 1/3681; A61M 1/369; A61M 1/32; A61M 2001/3431; A61M 1/342; A61M 1/3472; A61M 1/3633; A61M 2205/05; A61M 1/3672; A61M 2202/206; A61M 1/14; A61M 1/3687; A61M 1/38; A61M 2202/0208; A61M 2202/0225; A61M 2202/0266; A61M 2202/0258; A61M 2202/025; A61M 2202/0233; A61M 2202/0275; A61M 2202/0283; A61M 2202/0291; A61M 1/3621; A61M 2202/20; A61M 2202/203; A61K 35/14; A61L 2/0017; A61L 2/0047; A61L 2/0064; A61L 2/007; A61L 2/0076; Y10S 128/03; Y10S 261/28
USPC ........... 604/4.01, 5.01, 5.02, 5.04, 6.01, 6.07, 604/6.08, 6.09, 6.14, 6.15; 422/44, 45; 424/618; 514/2.9, 2.3, 2.4, 2.7, 2.8, 29
See application file for complete search history.

(56) References Cited

U.S. PATENT DOCUMENTS

| 4,950,225 A | 8/1990 | Davidner et al. |
| 5,104,373 A | 4/1992 | Davidner et al. |

(Continued)

FOREIGN PATENT DOCUMENTS

| WO | 2012/094671 | 7/2012 |
| WO | 2013106443 | 7/2013 |

OTHER PUBLICATIONS

Klein et al., "Hospitalizations and Deaths Caused by Methicillin-Resistant *Staphylococcus aureus*, United States, 1999-2005", Emerging Infectious Diseases, 2007, 13(12):1840-1846.

(Continued)

*Primary Examiner* — Adam Marcetich
(74) *Attorney, Agent, or Firm* — Kilpatrick Townsend & Stockton LLP

(57) ABSTRACT

Extracorporeal systems and methods for treating blood-borne diseases in a subject or for developing drugs to treat blood-borne diseases include various environmental and treatment modules that can be tailored to a specific disease or infection. In certain embodiments of the systems and methods, a blood sample is treated with hydrostatic pressure, a pulsed electrical field, a pharmaceutical agent, microwave, centrifugation, sonification, radiation, or a combination thereof, under environmental conditions that are effective for the treatment.

43 Claims, 13 Drawing Sheets

Extracorporeal Treatment System

(51) Int. Cl.
*A61M 1/34* (2006.01)
*A61M 1/36* (2006.01)
*A61K 35/14* (2015.01)
*A61N 5/00* (2006.01)
*A61M 1/32* (2006.01)

(52) U.S. Cl.
CPC .............. *A61M 1/369* (2013.01); *A61M 1/3621* (2013.01); *A61M 1/3687* (2013.01); *A61N 5/00* (2013.01); *A61M 1/1698* (2013.01); *A61M 1/32* (2013.01); *A61M 1/3633* (2013.01); *A61M 1/3672* (2013.01); *A61M 2202/025* (2013.01); *A61M 2202/0208* (2013.01); *A61M 2202/0225* (2013.01); *A61M 2202/0233* (2013.01); *A61M 2202/0258* (2013.01); *A61M 2202/0266* (2013.01); *A61M 2202/0275* (2013.01); *A61M 2202/0291* (2013.01); *A61M 2202/20* (2013.01); *A61M 2205/05* (2013.01)

(56) References Cited

U.S. PATENT DOCUMENTS

| | | | | |
|---|---|---|---|---|
| 5,837,736 | A | * | 11/1998 | Mitchell et al. ............... 424/718 |
| 5,876,663 | A | | 3/1999 | Laroussi |
| 5,929,031 | A | * | 7/1999 | Kerwin et al. ............... 514/13.4 |
| 6,087,087 | A | * | 7/2000 | Yonetani et al. ................... 435/2 |
| 6,180,824 | B1 | * | 1/2001 | Stamler et al. ................ 562/507 |
| 6,193,681 | B1 | * | 2/2001 | Davidner et al. ............ 604/6.08 |
| 7,135,195 | B2 | | 11/2006 | Holladay et al. |
| 7,531,133 | B2 | | 5/2009 | Hole et al. |
| 2002/0033181 | A1 | * | 3/2002 | Groth et al. ................... 128/898 |
| 2002/0095108 | A1 | * | 7/2002 | Tsuchida et al. ............. 604/6.08 |
| 2002/0127317 | A1 | * | 9/2002 | Hotchkiss et al. ............. 426/474 |
| 2003/0026877 | A1 | | 2/2003 | Ruan et al. |
| 2003/0049809 | A1 | | 3/2003 | Kaiser et al. |
| 2003/0180421 | A1 | | 9/2003 | Ruan et al. |
| 2004/0022669 | A1 | | 2/2004 | Ruan et al. |
| 2004/0081580 | A1 | * | 4/2004 | Hole et al. ....................... 422/44 |
| 2004/0146602 | A1 | * | 7/2004 | Garwood et al. ................ 426/35 |
| 2005/0182349 | A1 | * | 8/2005 | Linde et al. ................... 604/4.01 |
| 2005/0242033 | A1 | | 11/2005 | Tu et al. |
| 2006/0037542 | A1 | | 2/2006 | Denes et al. |
| 2006/0084158 | A1 | | 4/2006 | Viol et al. |
| 2006/0134186 | A1 | | 6/2006 | Carlton et al. |
| 2006/0207594 | A1 | * | 9/2006 | Stenzler et al. .......... 128/204.18 |
| 2006/0244386 | A1 | | 11/2006 | Hooke et al. |
| 2006/0257877 | A1 | | 11/2006 | Anderle et al. |
| 2007/0014688 | A1 | * | 1/2007 | Hole et al. ....................... 422/44 |
| 2007/0144515 | A1 | * | 6/2007 | Stenzler et al. .......... 128/203.25 |
| 2008/0085329 | A1 | * | 4/2008 | Roth et al. ...................... 424/701 |
| 2008/0247904 | A1 | | 10/2008 | Paskalov |
| 2009/0060890 | A1 | * | 3/2009 | Humes et al. .............. 424/93.71 |
| 2009/0166298 | A1 | | 7/2009 | Fender |
| 2010/0217173 | A1 | | 8/2010 | Hyde et al. |
| 2010/0268199 | A1 | * | 10/2010 | Hyde et al. .................. 604/891.1 |
| 2010/0284867 | A1 | | 11/2010 | Konesky |
| 2010/0297200 | A1 | * | 11/2010 | Schoenfisch et al. ......... 424/401 |
| 2010/0331753 | A1 | * | 12/2010 | Gandini ....................... 604/5.02 |
| 2012/0046602 | A1 | | 2/2012 | Morfill et al. |
| 2013/0053762 | A1 | | 2/2013 | Rontal |
| 2013/0178834 | A1 | * | 7/2013 | Greenberg et al. ............ 604/522 |

OTHER PUBLICATIONS

International Application No. PCT/US2012/020651, "International Preliminary Report on Patentability", Jul. 18, 2013, 9 pages.
International Application No. PCT/US2012/020651, "International Search Report and Written Opinion", Aug. 17, 2012, 5 pages.
U.S. Appl. No. 13/737,930, "Non-Final Office Action" dated Dec. 5, 2014.
International Application No. PCT/US2013/020851, International Preliminary Report on Patentability mailed on Jul. 24, 2014, 11 pages.
International Application No. PCT/US2013/020851, International Search Report & Written Opinion mailed on May 15, 2013, 15 pages.
U.S. Appl. No. 13/737,930, "Final Office Action" mailed Jun. 12, 2015, 16 pages.

* cited by examiner

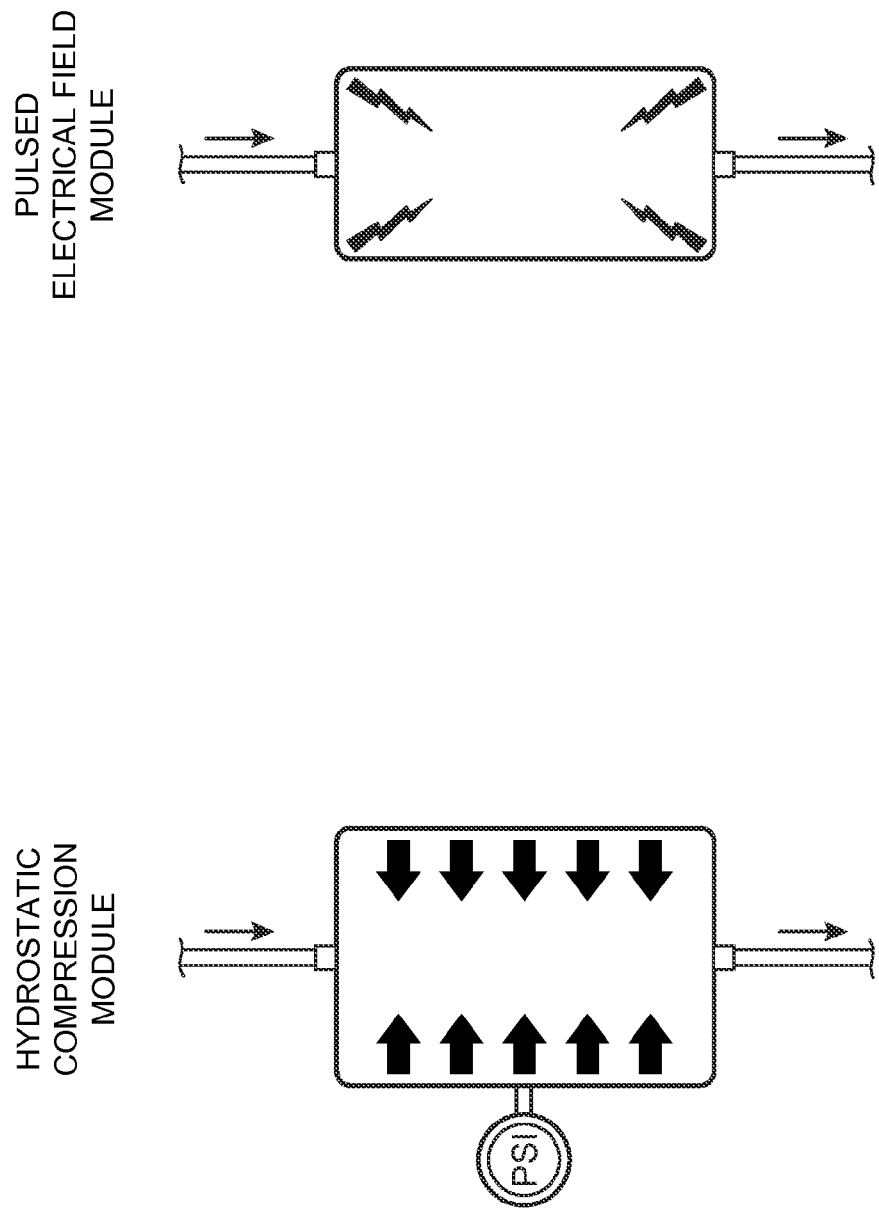

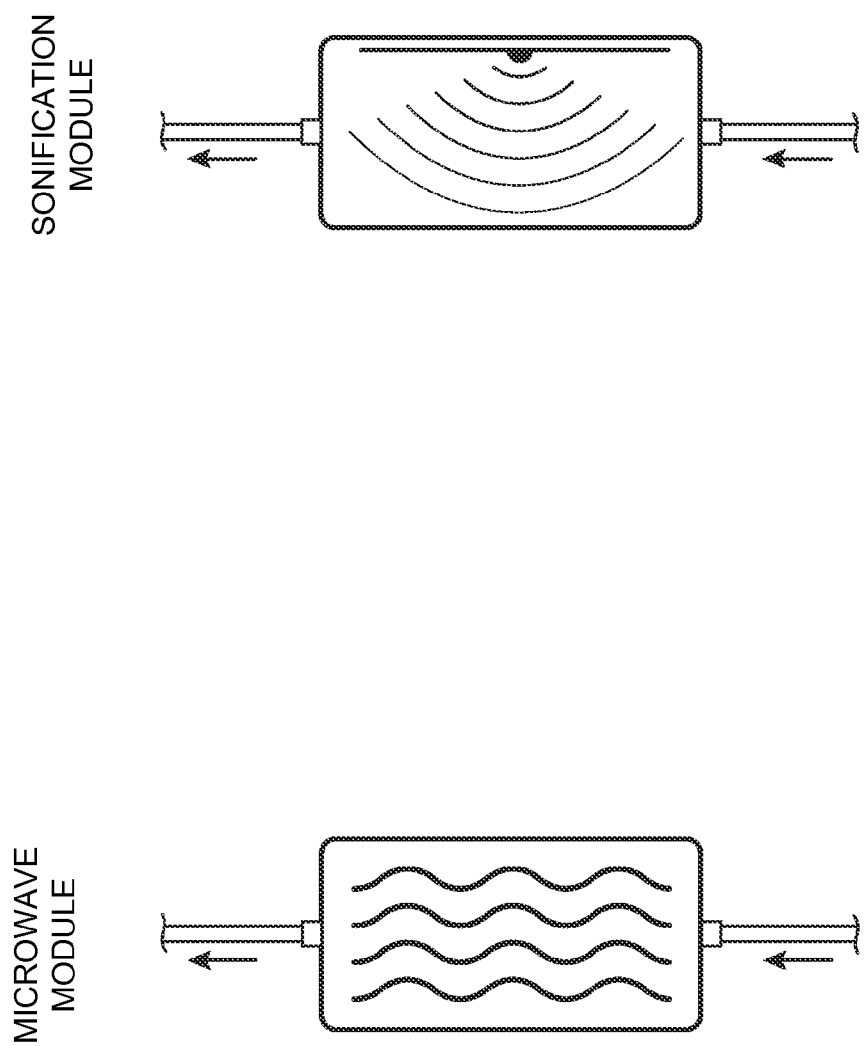

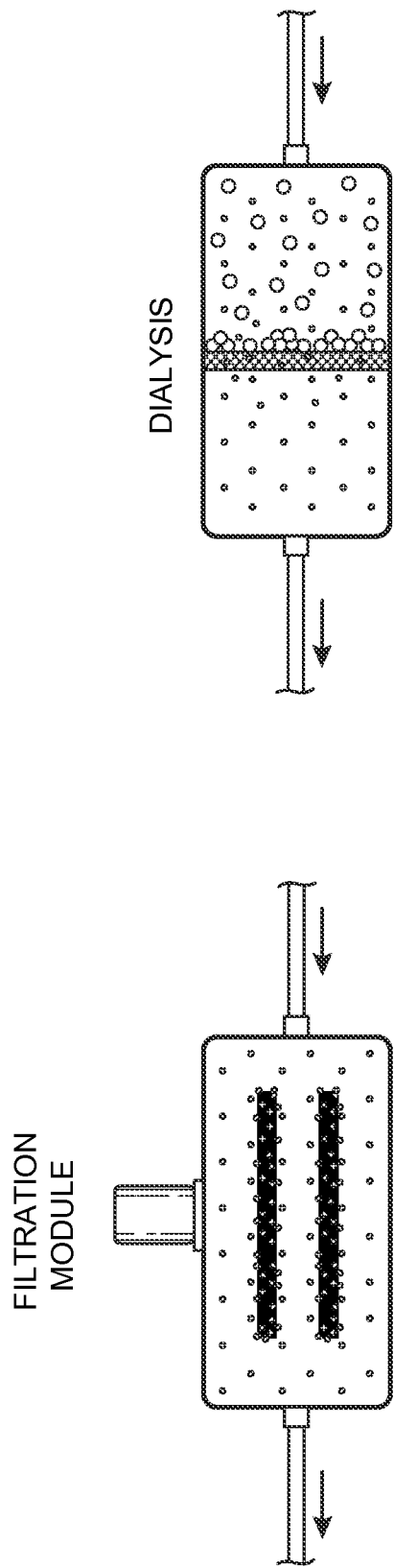

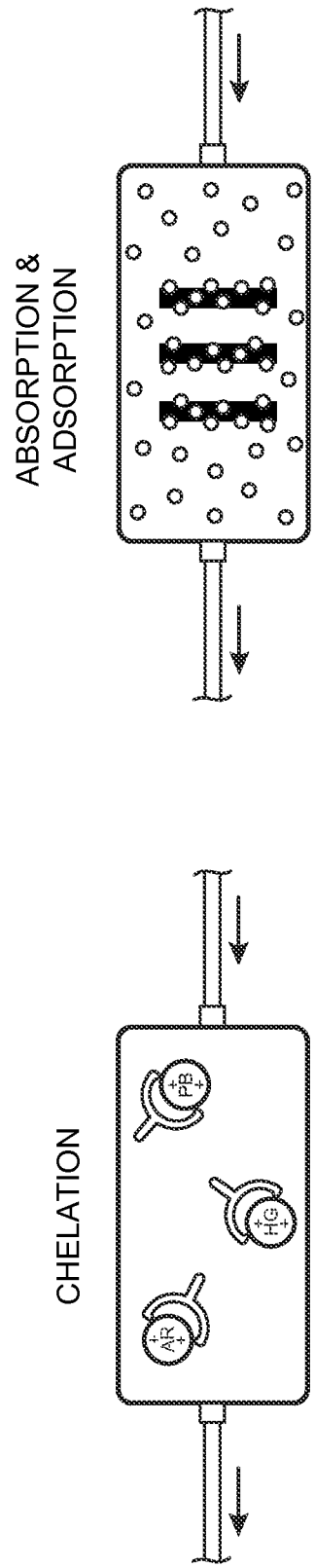

Extracorporeal Treatment System for Anthrax

FIG. 15

MODULAR EXTRACORPOREAL SYSTEMS AND METHODS FOR TREATING BLOOD-BORNE DISEASES

PRIOR RELATED APPLICATIONS

This application claims priority to U.S. provisional application No. 61/430,634, filed Jan. 7, 2011, the contents of which are hereby incorporated by reference in their entirety.

BACKGROUND OF THE INVENTION

The treatment of blood-borne disease by pharmacological intervention is limited by pathogen resistance and drug toxicity; the drugs used to attack pathogens are often also toxic to healthy human cells and tissues. Pharmaceutical intervention is also limited by the constant and rapid evolution of pathogens, especially bacteria, to adapt and become resistant to drugs. Methicillin-resistant *Staphylococcus aureus* ("MRSA") is especially pernicious and is gaining national and worldwide attention as a priority for disease control efforts. A 2007 report in Emerging Infectious Diseases, a publication of the Centers for Disease Control and Prevention (CDC), estimated the number of MRSA infections in hospitals doubled nationwide, from approximately 127,000 in 1999 to 278,000 in 2005, while at the same time annual deaths increased from 11,000 to more than 17,000. Klein E, Smith D L, Laxminarayan R (2007), "Hospitalizations and Deaths Caused by Methicillin-Resistant *Staphylococcus aureus*, United States, 1999-2005," Emerg. Infect. Dis. 13(12):1840-6. However, most large pharmaceutical companies in the United States have abandoned basic research and development of new antibiotic drugs and are focusing their research and development efforts elsewhere, despite the ever growing problem of antibiotic resistance.

Accordingly, there is a need to develop systems and methods to efficiently and effectively treat blood-borne diseases while minimizing toxicity to the patient. There is also a need in the art for methods of combating resistant pathogens in a patient, either by remodeling currently existing pharmaceutical interventions and/or by developing new and effective drugs and/or physical agents. Also needed are systems and methods to evaluate the efficacy of new antimicrobial drugs and physical agents under specific conditions, as well as to evaluate the safe use of antimicrobial drugs and treatment methods that were previously found to be effective against microbial pathogens but that were deemed too toxic for in vivo use.

SUMMARY OF THE DISCLOSURE

The invention meets one or more of these needs by providing systems and methods to efficiently and effectively treat blood-borne diseases while minimizing toxicity to the patient; methods of combating resistant pathogens in a patient by allowing for the use of currently existing drugs at levels not possible through current in vivo treatment and by developing new drugs or agents; and systems and methods to evaluate the efficacy of new antimicrobial drugs and physical agents under specific conditions, as well as to evaluate the safe use of antimicrobial drugs and treatment methods that were previously found to be effective against microbial pathogens but that were deemed too toxic for in vivo use.

The invention may be implemented in a number of ways.

In one aspect, extracorporeal methods for treating a blood-borne disease include the steps of removing blood from a subject; contacting the blood with an anticoagulant; optionally separating the blood into two or more blood fractions; modifying the environment of the blood or blood fraction; treating the blood or blood fraction with hydrostatic pressure, a pulsed electrical field, a pharmaceutical agent, centrifugation, radiation, microwave, sonification, or a combination thereof; and returning at least a portion of the blood or blood fraction to the subject. In some embodiments, the anticoagulant is heparin or sodium citrate. In certain embodiments, the blood is separated into a red blood cell fraction, a buffy coat fraction, a platelet fraction, a plasma fraction, or a combination thereof. In certain embodiments, some or all of the buffy coat portion is not returned to the subject. In some embodiments, the step of modifying the environment of the blood or a blood fraction comprises at least one of modifying the pH, modifying the temperature, modifying the oxygenation, modifying the available nutrients, modifying the carbon dioxide, modifying the osmolality, or a combination thereof.

In some embodiments, the modifying the environment step comprises lowering the pH, and the treating step comprises treating the blood or blood fraction with a pharmaceutical agent is that is acidic. The step of lowering the pH may comprise, for example, contacting the blood or blood fraction with carbonic acid, citric acid, hydrochloric acid, lactic acid, acetic acid, pyruvic acid, or a combination thereof. In other embodiments, the modifying the environment step comprises increasing the pH of the blood or blood fraction, and the treating step comprises treating the blood or blood fraction with a pharmaceutical agent that is basic. The step of increasing the pH may comprise, for example, contacting the blood with bicarbonate.

In certain embodiments, the temperature is modified to increase the replication rate of the pathogen. In certain embodiments, the modifying the environment step comprises reducing the blood or blood fraction temperature to about 30° C. to about 36° C. In other embodiments of the methods, the modifying the environment step comprises increasing the blood or blood fraction temperature to about 37° C. to about 42° C. In some embodiments, the modifying the environment step comprises oxygenating the blood or blood fraction. In other embodiments, the modifying the environment step comprises deoxygenating the blood or blood fraction.

The extracorporeal methods of the invention may include one or more additional step such as a treating step that comprises treating the blood or blood fraction with a pharmaceutical agent that is effective in anaerobic conditions, such as, but not limited to, metronidazole, clindamycin, chloramphenicol, or combinations thereof.

In certain embodiments, the methods may include the additional steps of modifying the environment of the treated blood or blood fraction by oxygenating the treated blood or blood fraction; and then administering to the blood or blood fraction a pharmaceutical agent effective in aerobic conditions, such as, but not limited to, daptomycin, azithromycin, silver, or combinations thereof.

In some embodiments, the step of modifying the environment comprises adding glucose to the blood or blood fraction. In other embodiments, the step of modifying the environment comprises reducing glucose in the blood or blood fraction.

In some embodiments, the step of modifying the environment comprises increasing the carbon dioxide in the blood or blood fraction. In certain embodiments, the treating step comprises treating the blood or blood fraction with hydrostatic pressure at a pressure range from about 50 MPa to about 1,000 MPa. In certain embodiments, the step of modifying the environment also comprises reducing the temperature of the blood or blood fraction, and the treating step comprises treating the blood or blood fraction with hydrostatic pressure.

In some embodiments, the treating step comprises treating the blood or blood fraction with a pulsed electrical field and a pharmaceutical agent. In certain embodiments, the step of modifying the environment comprises reducing the blood or blood fraction temperature, and the treating step comprises treating the blood or blood fraction with a pulsed electrical field and a pharmaceutical agent.

In some embodiments of the methods, the step of modifying the environment comprises reducing the blood or blood fraction temperature, and the treating step comprises treating the blood or blood fraction with microwaves.

In some embodiments of the methods, the treating step comprises treating the blood or blood fraction solely by centrifugation and removal of the pathogen and/or infected cells.

In some embodiments, the treating step comprises irradiating the blood or blood fraction by exposing the blood or blood fraction to X-ray, UV, IR, visible, laser, radiofrequency energy, or a combination thereof. In certain embodiments, the step of irradiating the blood or blood fraction comprises exposing the blood or blood fraction to about 50 to about 75 gray units.

In another aspect, the extracorporeal treatment methods of the invention further comprise a step of removing toxins from the blood or blood fraction before or after the treating step. The step of removing toxins may comprise, for example, filtering the blood or blood fraction, dialyzing the blood or blood fraction, chelating the blood or blood fraction, absorbing toxins from the blood or blood fraction, or a combination thereof. In certain embodiments, the filtering step comprises directing the blood through a filter having an average pore size of about 0.3 to about 1.5 microns. In other embodiments, the filtering step comprises directing the blood through an antibody capture module. In certain embodiments, an antibody capture module may comprise monoclonal antibodies with magnetic nanoparticles.

In any of these aspects, the extracorporeal method can also include the additional steps of: modifying the environment of the treated blood or a blood fraction; treating the blood or blood fraction with hydrostatic pressure, a pulsed electrical field, a pharmaceutical agent, microwave, centrifugation, radiation, sonification, or a combination thereof; and optionally repeating these steps.

In another aspect, methods for the extracorporeal treatment of MRSA include the steps of removing blood from a subject; contacting the blood with an anticoagulant; separating the blood into red blood cell, buffy coat, and plasma fractions; treating the red blood cell fraction with at least one pharmaceutical module; treating the plasma fraction with a radiation module; subjecting both the red blood cell fraction and the plasma fraction to a filtration module; and returning at least a portion of the blood or blood fraction to the subject. In some embodiments, the at least one pharmaceutical module delivers silver ions. In some embodiments, the pharmaceutical module is combined with a pulsed electrical field module to deliver gentamicin and daptomycin. In some embodiments, the pharmaceutical module is combined with a pulsed electrical field module to deliver metronidazole and clindamycin under anaerobic conditions. In some embodiments, the methods include three pharmaceutical modules including one that delivers silver ions, one that is combined with a pulsed electrical field module to deliver gentamicin and daptomycin, and one that is combined with a pulsed electrical field module to deliver metronidazole and clindamycin under anaerobic conditions In another aspect, methods for the extracorporeal treatment of *Bacillus anthracis* include the steps of removing blood from a subject; contacting the blood with an anticoagulant; separating the blood into red blood cell, buffy coat, and plasma fractions; treating the red blood cell fraction with at least one pharmaceutical module; treating the plasma fraction with a high hydrostatic pressure module; subjecting both the red blood cell fraction and the plasma fraction to a filtration module; and returning at least a portion of the blood or blood fraction to the subject. In some embodiments the pharmaceutical module delivers a high dose of cisplatin, mevastatin, or tetracyclines. In other embodiments, the pharmaceutical module is used in combination with a high hydrostatic compression module to deliver a high dose of a quinolone antibiotic. In some embodiments, the methods include four pharmaceutical modules including one that delivers cisplatin, one that delivers mevastatin, one that delivers tetracyclines, and one that is combined with an HHP module to deliver a quinolone antibiotic.

In another aspect, methods for the extracorporeal treatment of malaria include the steps of removing blood from a subject; contacting the blood with an anticoagulant; separating the blood into red blood cell, buffy coat, and plasma fractions; treating the red blood cell fraction with at least one pharmaceutical module; treating the plasma fraction with a microwave module; subjecting both the red blood cell fraction and the plasma fraction to a filtration module; and returning at least a portion of the blood or blood fraction to the subject. In some embodiments the pharmaceutical module delivers a high dose of quinine, clindamycin, artemether, doxycycline, or a combination thereof. In other embodiments, the pharmaceutical module is used in combination with a low energy microwave module. In some embodiments, the methods include three pharmaceutical modules including one that delivers quinine and clindamycin, one that delivers artemether, and one that delivers doxycycline.

In another aspect, methods for the extracorporeal treatment of hemorrhagic fever include the steps of removing blood from a subject; providing the subject with replacement platelets, white blood cells, red blood cells, and/or saline; contacting the removed blood with an anticoagulant; separating the blood into red blood cell, buffy coat, and plasma fractions; treating the red blood cell fraction with at least one pharmaceutical module; treating the plasma fraction with a radiation module; subjecting both the red blood cell fraction and the plasma fraction to a filtration module; and returning at least a portion of the blood or blood fraction to the subject.

In another aspect of the invention, extracorporeal systems include a blood removal port; an anticoagulant module; a module adapted to modify the environment of blood or a blood fraction; at least one treatment module adapted to administer hydrostatic pressure, a pulsed electrical field, a pharmaceutical agent, microwave, centrifugation, or a combination thereof; and a blood return port. In some embodiments, the module for modifying the environment comprises an environmental module. In certain embodiments, the environmental module comprises at least one of a pH modifying module, a deoxygenation module, and a temperature control module. In certain embodiments, the environmental module is a pH-modifying module, and wherein the treatment module is adapted to administer a pharmaceutical agent that is effective at a certain pH range. In certain other embodiments, the environmental module deoxygenates the blood or blood fraction, and wherein the treatment module is adapted to administer a pharmaceutical agent that is effective in anaerobic conditions. In other embodiments, the environmental module decreases the temperature of the blood or blood fraction, and wherein the treatment module is adapted to administer hydrostatic pressure, a pulsed electrical field, or a combination thereof.

In another aspect, systems for the extracorporeal treatment of MRSA may include a blood removal port; an anticoagulant module; a separation module; a module adapted to modify the environment of blood or a blood fraction; at least one treatment module adapted to administer a pharmaceutical agent, pulsed electric field, radiation, or a combination thereof; a filtration module; and a blood return port.

In another aspect, systems for the extracorporeal treatment of *Bacillus anthracis* may include a blood removal port; an anticoagulant module; a separation module; a module adapted to modify the environment of blood or a blood fraction; at least one treatment module adapted to administer hydrostatic pressure, a pharmaceutical agent, or a combination thereof; a filtration module; and a blood return port.

In another aspect, systems for the extracorporeal treatment of malaria may include a blood removal port; an anticoagulant module; a separation module; a module adapted to modify the environment of blood or a blood fraction; at least one treatment module adapted to administer a pharmaceutical agent, microwave, or a combination thereof; a filtration module; and a blood return port.

In another aspect, systems for the extracorporeal treatment of hemorrhagic fever may include a blood removal port; an anticoagulant module; a separation module; a module adapted to modify the environment of blood or a blood fraction; at least one treatment module adapted to administer a pharmaceutical agent, radiation, or a combination thereof; a filtration module; and a blood return port.

In another aspect of the invention, methods for developing a new drug or treatment regimen in an extracorporeal system for the treatment of a subject include the steps of obtaining a blood sample that contains a known concentration of pathogens; optionally separating the blood sample into a red blood cell fraction, a buffy coat fraction, a plasma fraction, or a combination thereof; modifying the environment of at least a portion of the blood sample or a blood fraction; treating the blood sample or blood fraction with hydrostatic pressure, a pulsed electrical field, a pharmaceutical agent, microwave, centrifugation, radiation, sonification, or a combination thereof; and determining the concentration of pathogens in the blood sample or blood fraction after the treating step, wherein the treatment is successful for the pathogen if it eliminates or reduces the concentration of the pathogens in the blood sample or blood fraction when compared to the known original concentration in the sample. In certain embodiments, these methods further include the step of treating a subject with the drug or treatment determined to be successful in the extracorporeal system.

In another aspect of the invention, extracorporeal systems for developing a new drug or treatment regimen for the extracorporeal treatment of a subject include a first blood or blood fraction collection chamber with a first inlet and a first outlet port; an anticoagulant module; a module to modify the environment of the blood or blood fraction; at least one treatment module that is adapted to administer hydrostatic pressure, a pulsed electrical field, a pharmaceutical agent, microwave, centrifugation, radiation, sonification, or a combination thereof to the blood or blood fraction; and a second blood or blood fraction collection chamber with a second inlet port and a second outlet port. In certain embodiments, the extracorporeal systems further include a module to separate the blood or blood fraction into a red blood cell fraction, a buffy coat fraction, a plasma fraction, or a combination thereof; In certain embodiments, the extracorporeal systems further include a sensor to determine the concentration of pathogens in the blood sample or blood fraction in the second blood or blood fraction collection chamber.

In another aspect of the invention, methods for treatment of a blood sample or blood fraction prior to transfusion to a subject include the steps of obtaining a blood sample or blood fraction; optionally separating the blood sample or blood fraction into a red blood cell fraction, a buffy coat fraction, a plasma fraction, or a combination thereof; modifying the environment of at least a portion of the blood sample or the blood fraction; treating the blood sample or blood fraction with hydrostatic pressure, a pulsed electrical field, a pharmaceutical agent, microwave, centrifugation, radiation, sonification, or a combination thereof; and determining the concentration of pathogens in the blood sample or blood fraction after the treating step.

In another aspect, extracorporeal systems for the treatment of a blood sample or blood fraction prior to transfusion to a subject include a first blood or blood fraction collection chamber with a first inlet and a first outlet port; an anticoagulant module; an optional module to separate the blood or blood fraction into a red blood cell fraction, a buffy coat fraction, a plasma fraction, or a combination thereof; a module to modify the environment of the blood or blood fraction; at least one treatment module that is adapted to administer hydrostatic pressure, a pulsed electrical field, a pharmaceutical agent, microwave, centrifugation, radiation, sonification, or a combination thereof to the blood or blood fraction; and a second blood or blood fraction collection chamber with a second inlet port and a second outlet port. These systems may, in certain embodiments, also include a sensor to determine the concentration of pathogens in the blood sample or blood fraction in the second blood or blood fraction collection chamber.

In another aspect of the invention, devices for use in the systems or methods disclosed herein are provided.

Additional features, advantages, and embodiments of the invention may be set forth or apparent from consideration of the following detailed description and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, and illustrate embodiments of the invention and together with the detailed description serve to explain the principles of the invention. No attempt is made to show structural details of the invention in more detail than may be necessary for a fundamental understanding of the invention and various ways in which it may be practiced.

FIGS. 4 to 9 are schematic drawings that illustrate exemplary treatment modules of the invention. FIG. 4 is a schematic drawing showing an expanded view of an exemplary pharmaceutical module of the invention to administer an antimicrobial drug. Certain pharmaceutical agents require longer exposure times in order to be effective against certain pathogens. Therefore, the coil shown in this drawing reflects an example of one embodiment in which a longer exposure time to a pharmaceutical agent may be achieved. Similar extended exposure times may be achieved by any methods known in the art such as, for example, directing the fluids to a reservoir or other container in order to expose the pathogen for a particular period of time before moving to the next treatment or module.

FIG. 5 is a schematic drawing that illustrates an expanded view of an exemplary radiation module of the invention. This module may be disposed after a separation module in which the blood is separated into a plasma component and a blood cell component. The plasma component may be subjected to UV radiation, whereas the cellular component may be subjected to X-ray radiation.

FIG. 6 is a schematic drawing that illustrates an expanded view of one embodiment of an exemplary high hydrostatic pressure (HHP) module of the invention.

FIG. 7 is a schematic drawing that illustrates an expanded view of one embodiment of an exemplary pulsed electrical field module of the invention.

FIG. 8 is a schematic drawing that illustrates an expanded view of one embodiment of an exemplary microwave module of the invention.

FIG. 9 is a schematic drawing that illustrates an expanded view of one embodiment of an exemplary sonification module of the invention.

FIGS. 10 to 13 are schematic drawings illustrating several exemplary toxin removal modules of the invention. FIG. 10 is a schematic drawing that illustrates an expanded view of one embodiment of an exemplary filtration module of the invention. In this embodiment, the filtration module comprises a disposable polymyxin cartridge FIG. 11 is a schematic drawing that illustrates an expanded view of an exemplary dialysis module of the invention.

FIG. 12 is a schematic drawing that illustrates an expanded view of an exemplary chelation module of the invention.

FIG. 13 is a schematic drawing that illustrates an expanded view of an exemplary adsorption/absorption module of the invention.

Figure 15:
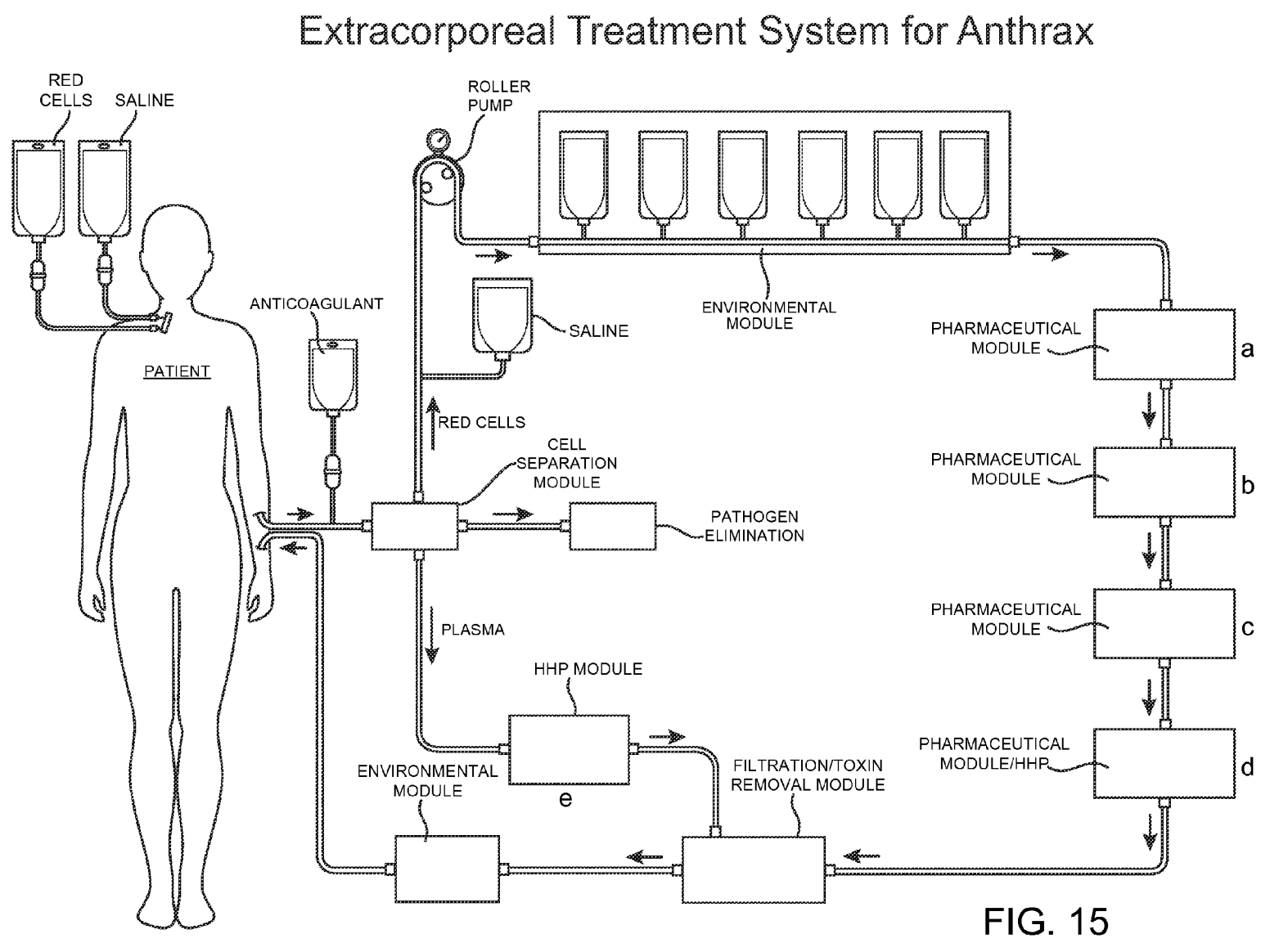

FIG. 15 is a schematic drawing that illustrates an exemplary embodiment of an extracorporeal system of the invention particularly designed for the treatment of *Bacillus anthracis* (anthrax). This embodiment includes an anticoagulant module, a separation module to separate the blood into a red blood cell fraction, a plasma fraction, and a buffy coat fraction comprising some of the pathogen (which is discarded and not returned to the patient). The red blood cell fraction is then subjected to a pretreatment environmental module and a pharmaceutical module for the delivery of a high dose of cisplatin to inactivate lethal anthrax toxins (shown as component a). The red blood cell fraction is also treated with another pharmaceutical module to deliver mevastatin to attenuate the anthrax infection progression (shown as component b), as well as another pharmaceutical module to deliver tetracyclines, animal derived peptides, to kill both anthrax bacilli and spores (shown as component c). The red blood cell fraction is treated with a combination of a pharmaceutical module designed and a high hydrostatic pressure (HHP) module for treatment with a high dose of quinolone antibiotic along with low level HHP for the synergistic killing of bacilli and spores (shown as component d). The plasma fraction is subjected to an HHP module with high level HHP to sterilize the plasma of all bacilli and spores (shown as component e). Both the plasma fraction and the red blood cell fraction are filtered to remove pathogens and/or endotoxins, before proceeding to a post-treatment environmental module and returning to the patient.

DETAILED DESCRIPTION OF THE INVENTION

Figure 1:
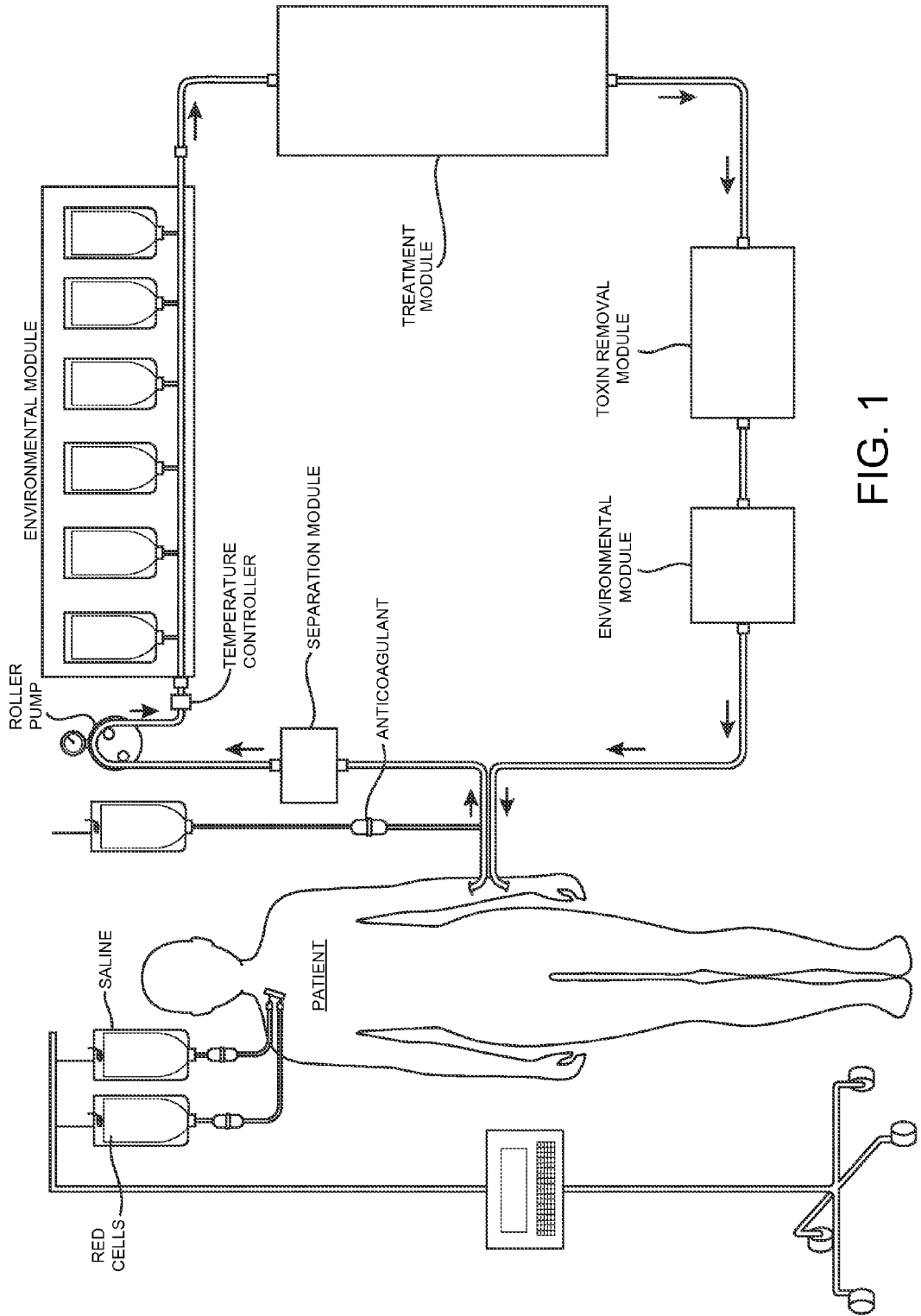
FIG. 1 is a schematic drawing illustrating an extracorporeal system constructed according to the principles of the invention including an anticoagulant module, a separation module, a temperature control module, a first environmental module (as a pretreatment module, expanded in this drawing to show several potential environmental modules), a treatment module, a toxin removal module, and a second environmental module (as a posttreatment module before the blood, blood fraction, or a portion thereof is returned to the patient). Both environmental modules may include one or more modules for modifying the environment of the blood or blood fraction, as discussed in detail below. In addition, although the drawing includes the separation module prior to the first environmental module, in other embodiments the separation module may not be included in the system, may be included after the first environmental module and before the treatment module, or may be included as the treatment module.
Figure 2:
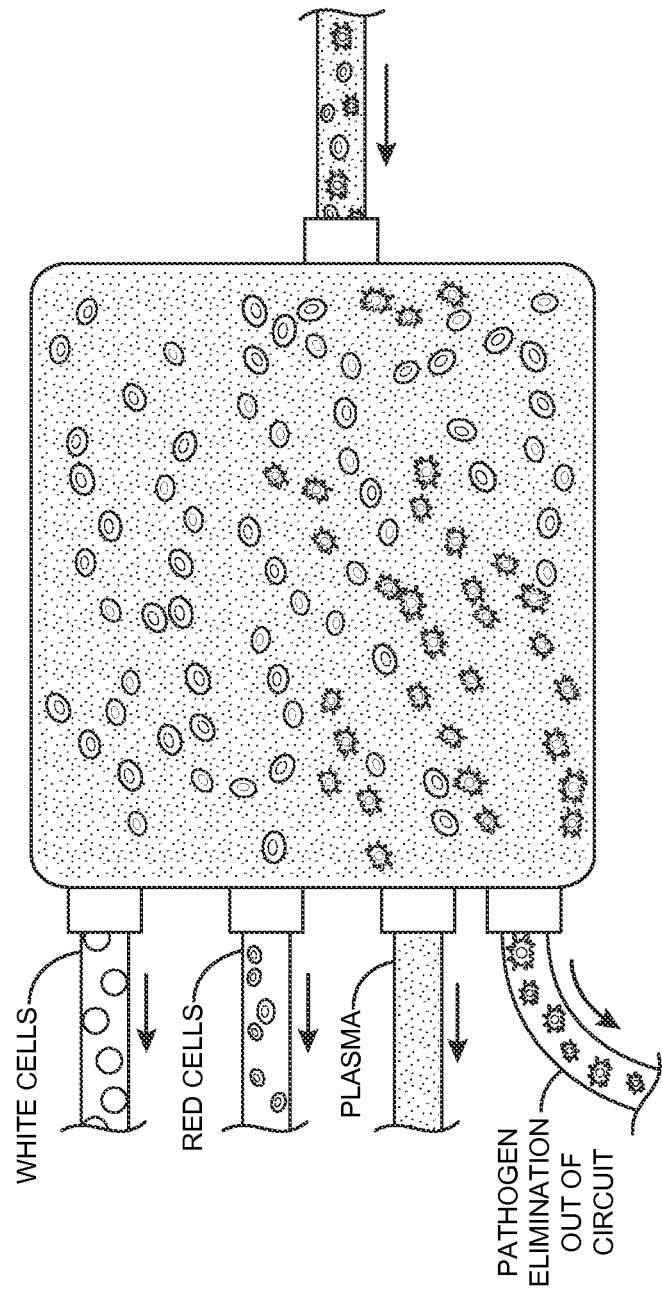
FIG. 2 is a schematic drawing that illustrates an expanded view of an exemplary separation module of the invention. This embodiment illustrates the separation of the blood into two or more different blood fractions, such as white blood cells, red blood cells, plasma, and pathogens. In certain embodiments, the pathogens are located with the buffy coat component after centrifugation, and the buffy coat/pathogen component is eliminated from the fluid prior to returning the blood or blood fraction or a part thereof to the patient. In certain embodiments, the separation module is used to separate white cells from other blood fractions, both for the purposes of treating hemorrhagic fevers and also to take advantage of new techniques available to enhance white cell function by extracorporeal treatments and then return the white blood cells to the circulation in the patient.

It is understood that the invention is not limited to the particular methodology, protocols, and mechanical features, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a drug" is a reference to one or more drugs and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

As used herein, the terms "subject" and "patient" are used interchangeably to refer to any animal capable of blood removal and return. The subject or patient is preferably a mammal, and is most preferably a human, but also may include laboratory, pet, domestic, or livestock animals.

Unless otherwise specified, the term "blood" refers to whole blood or any fraction(s) of whole blood including a red blood cell fraction, a buffy coat fraction, a platelet fraction, a plasma fraction, and any combination of two or more of these fractions.

As used herein, the term "pathogen" includes any invading microorganism including, but not limited to, bacteria, viruses, protozoa, fungi, prions, prion-like particles, and other parasites. In certain embodiments, the pathogen includes, but is not limited to, *Staphylococcus aureus, Escherichia coli, Streptococcus, Klebsiella, Enterobacter, Meningococcus, Treponema*, and other bacteria. In certain other embodiments, the pathogen includes, but is not limited to, a malarial parasite, a trypanosomal parasite, and other parasites. In yet other certain embodiments, the pathogen includes, but is not limited to, human immunodeficiency virus, hepatitis viruses A, B, C, D, and E, herpesvirus, human papillomavirus, arbovirus, human T-lymphotropic virus type I, and West Nile virus and other viruses.

"Blood-borne disease" includes any disease in which a pathogen or part thereof is located in the bloodstream. It can, but need not be a disease characterized by infection of the blood itself (such as septicemia), a neoplastic disease (such as a leukemia), or an immune disorder.

A "drug," "pharmaceutical agent," or "antimicrobial agent," as used herein, includes any small molecule, gas, or biologic agent effective to kill or impair one or more pathogens. Notably, pharmaceutical agents used herein do not require any minimum safety or toxicity threshold because they are not administered directly to the subject, but rather are administered extracorporeally. Accordingly, pharmaceutical agents may be used in the present methods at high concentrations for variable periods of time as required by the agent and pathogen. In addition, certain combinations of pathogen and drug(s) may require very high doses of the drug(s) to be delivered rapidly via pulsation techniques as opposed to steady state delivery of the drug to the pathogen over a period of time.

As used herein, the term "blood fraction" refers to a red blood cell fraction, a buffy coat fraction, a white blood cell fraction, a platelet fraction, a plasma fraction, or a combination thereof.

Embodiments of the invention provide modular extracorporeal methods and systems, whereby blood is removed from a subject, the blood is subjected to a customizable circuit of environmental, pharmaceutical, and non-pharmaceutical interventions, and finally the blood is returned to the subject. By moving the battlefield in the war against infection out of the body and into an extracorporeal system, many common patient toxicity problems experienced with conventional in vivo antimicrobial therapies will be reduced or eliminated. Because the extracorporeal system can control environmental conditions in a way not possible in vivo, the system will restore efficacy to drugs currently rendered ineffective by resistance, and also permit the use of drugs that may be effective against pathogens, but are intolerably toxic in vivo. In addition, the extracorporeal system can be used to treat blood (e.g., from a blood bank) for use in transfusion to a different subject to ensure that it is safe and free of pathogens. The extracorporeal system can also serve as a useful research tool for developing and screening new drugs and new drug classes and for optimizing the conditions under which the drugs are most effective.

Furthermore, the modular design of the device allows the treatment to be individually tailored to a specific patient or a specific pathogen (See, e.g., FIGS. 14-17 for examples of some embodiments of the disclosed systems for treatment of specific pathogens (although different combinations of modules are envisioned for each pathogen, in addition to the exemplary embodiments shown in these figures)). This aspect will complement the currently evolving techniques of rapid DNA-based identification of microbes, such as sepsis-producing organisms. It will now be possible to accurately identify and specifically attack blood pathogens. The modules can be selected, customized, and sequenced to provide an optimized course for a specific pathogen and/or to combat future mutations (e.g., resistance) of pathogens. In particular, the extracorporeal system can be used to create stressful environmental conditions to which the offending microbes have little or no evolutionary experience. Thus, future microbial resistance will be stymied. Without being bound by theory, the extracorporeal systems and methods described herein can be used, e.g., as follows to combat particular mechanisms of microbial resistance to pharmaceutical agents:

As a first mechanism, microorganisms develop the ability to actively pump or efflux antimicrobial drugs out of their systems. This pumping requires that the microbe expend energy to pump drugs out of their cells. The described methods, systems, and devices counteract this form of resistance by: a) administering a high concentration (e.g., higher than the dose tolerated in vivo) of pharmaceutical agents that set up a concentration gradient to force the diffusion of more drug into the microbial cells; b) adjusting pH to towards the pKa of the antimicrobial drug(s) to optimize both diffusion into, and ion-trapping within, the target cells; c) decreasing oxygen levels and/or decreasing glucose levels to force the microbes to resort to less efficient pathways of energy production, which reduces energy availability for efflux pumping and other resistance modes; and d) subjecting the blood or blood fraction to low levels of pulsed electrical field discharge to enhance the penetration of the pathogen by the antimicrobial agents and to defeat the active efflux pumping resistance mechanisms of the pathogen.

Second, microorganisms develop the ability to modify the structure of critical binding sites so that they have decreased affinity for pharmaceutical agents. This mechanism is similarly thwarted with the inventive principles because increasing the amount of drug inside the microbial cell (as described in a)-d) above with respect to the first mechanism) will partially compensate for decreased binding affinity of any particular critical binding site.

Third, microorganisms produce a profusion of unmodified non-critical binding sites that serve to decoy and divert pharmaceutical agents away critical binding sites. This mechanism is similarly thwarted with the inventive principles because increasing the amount of drug inside the microbial cell (as described in a)-d) above with respect to the first mechanism) will partially compensate for the profusion of decoy binding sites. Furthermore, the induction and production of large numbers of decoy binding sites is energy dependent, and the microbial cells will have been forced into a state of reduced efficiency of energy production by the modifying the controlled environment of the pathogen to contain low glucose levels and/or higher or lower oxygenation, for example.

Fourth, microorganisms produce enzymes that partially or completely inactivate pharmaceutical agents. This mechanism is similarly thwarted because increasing the amount of drug inside the microbial cell (as described in a)-d) above with respect to the first mechanism) will tax the capacity of inactivating enzymes. Furthermore, microbial enzyme induction and production are energy dependent, and the microbial cells have been forced into a state of reduced energy production by creating the low glucose and/or modulated oxygen level environments.

Additionally, using drugs that block protein synthesis (e.g., clindamycin) under anaerobic conditions will further degrade the pathogen's already distressed capacity to synthesize both antimicrobial drug inactivating enzymes as well as the very enzymes that must be produced to switch over to anaerobic and/or low glucose energy production.

Exemplary extracorporeal systems and methods of the invention for treatment and for drug screening are described in further detail below.

I. Modular Extracorporeal Systems and Methods for Treating Blood-Borne Diseases

As shown in the schematically exemplary illustrated embodiments of the figures, the invention provides modular extracorporeal systems and methods for using the same to treat blood-borne diseases. Exemplary blood-borne disease include, but are not limited to, bacteria diseases such as sepsis, *Staphylococcus, Escherichia coli*, MRSA, *Bacillus anthracis*, syphilis, brucellosis, leptospirosis, tick-borne relapsing fever, *Streptococcus, Klebsiella, Enterobacter, Meningococcus*, and *Treponema*; viral diseases such as HIV, hepatitis viruses A, B, C, D, and E, herpes, human papillomavirus, arbovirus, human T-lymphotropic virus type I, viral hemorrhagic fever, and West Nile virus; protozoan diseases such as malaria, babesiosis, and diseases caused by a trypanosomal parasite; fungal diseases such as coccidiomycosis and candidiasis; diseases caused by prions and prion-like particles such as Creutzfeldt-Jakob disease (CJD); blood borne neoplastic diseases such as the blast phase in leukemia; and diseases caused by other parasites such as worms and flukes.

A. Blood Removal

Blood can be removed from the subject by any conventional means, e.g., catheter or port, known in the art including those known for blood and plasma donation and transfusion, dialysis treatment, vascular access procedures, and intravenous therapies. The system can include a peripheral line or a central line. As needed for stabilization of the subject, volume replacement may be augmented by crystalloid solutions. Oxygenation capacity may be augmented (for the subject) as needed by blood transfusion or by semi-synthetic hemoglobin preparations.

B. Anti-Coagulant

The disclosed systems may involve providing an anti-coagulant to the blood after removal to ensure that the blood can circulate through the circuit essentially unimpeded by clotting. Any anticoagulant known in the art may be used including those known for dialysis and/or hemofiltration. In some embodiments, the anticoagulant is heparin or sodium citrate. When the anticoagulant is sodium citrate, addition of the anticoagulant module may also serve as the environmental module, as sodium citrate will modify the environment of the blood by modifying the pH.

C. Cell Separation and Pathogen Removal Module

The cell separation and pathogen removal module (also referred to herein as separation module) separates whole blood into two or more fractions. The separation module may be used in the present methods before or after an environmental module, treatment module, or toxin removal module, depending on the goal of the separation (e.g., separation of blood fractions to enable the most effective treatment without harm, or separating out particular pathogens from specific blood fractions). The blood fractions can be, for example, a red blood cell fraction, a buffy coat fraction, a platelet fraction, a plasma fraction, pathogen fraction(s), and any combination of two or more of these fractions. Separation can be accomplished by any method known in the art, such as those methods used by blood banks (centrifugal or filtration based). In another embodiment, separation utilizes tangential flow and/or immunological separation methods.

In certain embodiments, the separation module may be used as a treatment module. In one embodiment, separation is accomplished by low speed centrifugation, high speed centrifugation, or ultracentrifugation. In certain embodiments, the low speed centrifugation, high speed centrifugation, or ultracentrifugation is used to sequester pathogens according to their size and weight for removal from the extracorporeal circuit. Any centrifugation speed known in the art for separation of cell types may be used. In some embodiments, centrifugation at about 11,000 rpm to about 14,000 rpm, about 11,000 rpm to about 13,000 rpm, or about 12,000 rpm to about 14,000 rpm may be used to separate uninfected blood cells from infected blood cells. In certain embodiments, the samples are centrifuged at about 12,000 rpm to about 13,000 rpm. In other embodiments of the systems, high speed centrifugation at about 20,000 rpm to about 40,000 rpm, about 20,000 rpm to about 30,000 rpm, or about 30,000 to about 40,000 may be used to separate bacteria from blood cells. In certain embodiments, the samples are centrifuged at about 30,000 rpm. In other embodiments of the systems, ultracentrifugation at about 60,000 rpm to about 80,000 rpm, about 60,000 rpm to about 70,000 rpm, or about 70,000 rpm to about 80,000 rpm may be used to separate viruses from blood cells. In certain embodiments, centrifugation at about 70,000 rpm is used. Higher speeds may be used to separate out molecules that are smaller in size than viruses.

In one embodiment, a buffy coat fraction is separated from the whole blood. The buffy coat primarily consists of white cells and bacteria that spin out into a layer between the red blood cell fraction and the plasma fraction. The buffy coat fraction may be circulated through the extracorporeal system (alone or in combination with other blood fractions) and returned to the patient.

In another embodiment, the buffy coat fraction is separated from the whole blood and not returned to the patient. Without being bound by theory, the buffy coat fraction is believed to contain pathogens that have been engulfed or partially engulfed by white blood cells by phagocytosis. The engulfed pathogens pose a serious threat in vivo because they are largely protected from pharmaceuticals, e.g., antibiotics, until the engulfing white cell disintegrates thereby releasing the still viable and potentially drug-resistant pathogens back into the bloodstream. In septicemia, the majority of blood-borne bacteria will often be trapped in the buffy coat fraction. Accordingly, in one embodiment, the buffy coat fraction is isolated and discarded. By discarding the buffy coat fraction, the pathogen load of the blood returning to the patient can be significantly decreased. Moreover, destroying bacteria creates harmful endotoxins which themselves elicit an immune response. By removing the bacteria essentially intact, as opposed to destroying them within the extracorporeal circuit, endotoxin production and cytokine release is greatly reduced or eliminated, as is the need for larger amounts of toxic drugs. Although a large portion of the pathogen load may be eliminated by discarding the buffy coat fraction, the pathogen load may be further diminished by subjecting the remaining blood fractions to one or more treatment modules, in combination with one or more environmental modules.

Although there is a concomitant loss of white cells associated with buffy coat disposal, approximately 20% of the white cells will remain in the red blood cell fraction, and even more are in reserve within the patient's reticuloendothelial system and marginated along the vascular tree.

In another embodiment, the buffy coat fraction, or a sample thereof can be used for diagnostics using conventional equipment. For example, a sample of the buffy coat can be examined microscopically to identify the pathogen(s). With increasing advances in DNA-typing, it will be possible to use a buffy coat sample to definitively identify not only the generic type of pathogen, but the precise genotype of the strain and resistance pattern. This typing can guide the specific treatment needed for the further processing of the blood or blood fractions in the extracorporeal system disclosed herein to most effectively treat the particular pathogen(s) present.

D. Environmental Modules

One or more environmental modules (also referred to as "environmental control modules") can be included in the extracorporeal system. As used herein, the phrase "modifying the environment" of blood or a blood fraction refers to changing the conditions of the blood or blood fraction from the conditions under which the blood exists in the body, including, but not limited to, changing one or more external factors to affect the sample. For example, in certain embodiments, modifying the environment of blood or a blood fraction may include modifying the pH, modifying the temperature, modifying the oxygenation, modifying the available nutrients, modifying the carbon dioxide, modifying the osmolality, or a combination thereof.

The environmental module(s) can be included before the treatment module (as a "pre-treatment," as shown, e.g., in FIG. 1) or simultaneously with the treatment module, in order to provide the appropriate environment for a treatment module to be safe and effective. The environmental module(s) also may be interspersed between any two treatment modules, to ensure that the environment for each of the treatment modules is optimized for safety and efficacy. In addition, an environmental module may be included after any treatment modules to adjust the blood or blood fraction toward physiological conditions before returning the blood or blood fraction to the subject (as a "post-treatment," as shown, e.g., in FIG. 1).

Figure 3:
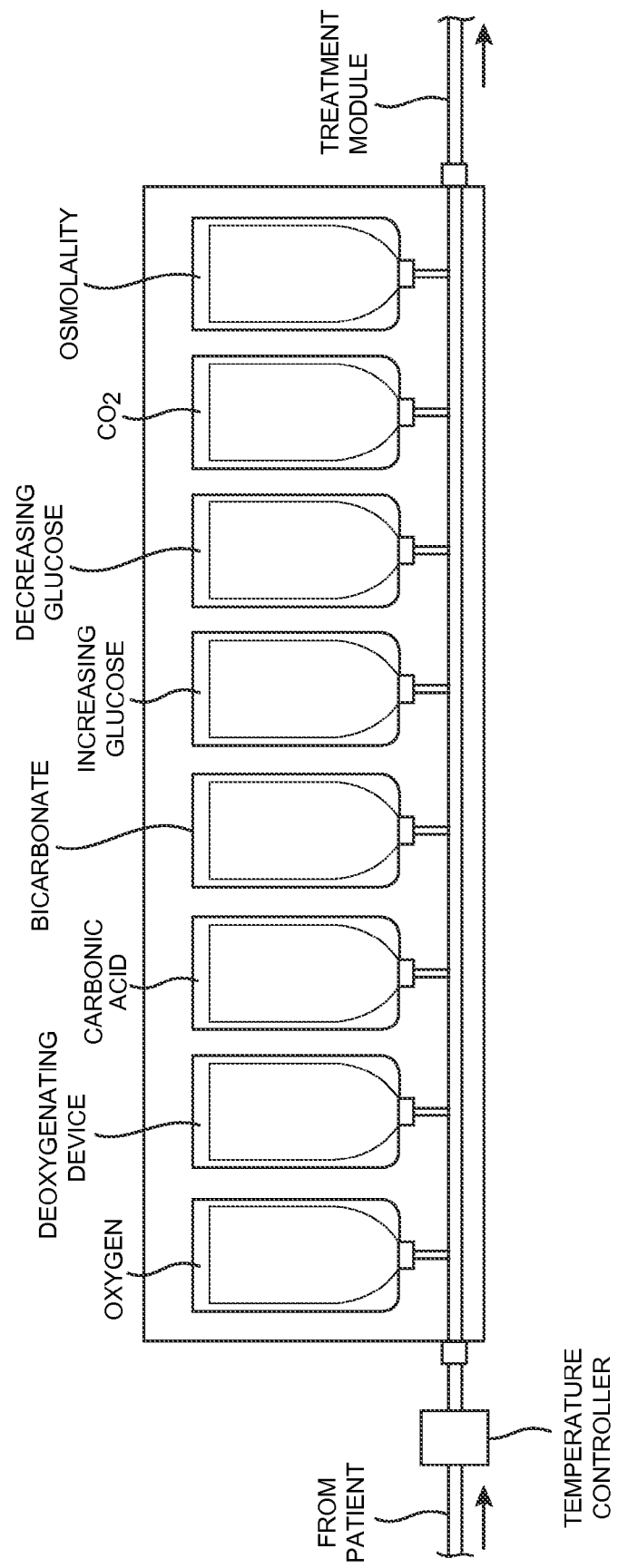
FIG. 3 is a schematic drawing that illustrates an expanded view of an exemplary environmental module of the invention. This embodiment includes a temperature control module, an oxygen control module (including an oxygenating component and deoxygenating component), pH control module (including pH-increasing component (bicarbonate) and pH-decreasing component (carbonic acid)), nutrient control module (including glucose-increasing component and glucose-decreasing component), carbon dioxide control module, and osmolality control module.

The environmental control modules can be included once, more than once, or not at all in the system, depending on the particular treatment method to be used. The invention also provides for sequential opposite modules, that is, a module that increases a particular property followed by one that decreases that property or vice versa. For example, FIG. 3 shows a module of high oxygen followed by a module of low oxygen or vice versa, a module of high glucose followed by a module of low glucose or vice versa, a module of high pH followed by a module of low pH or vice versa, and/or a module of high temperature followed by a module of low temperature or vice versa. These opposite modules can be coordinated to provide a module effecting aerobic conditions and a module effecting anaerobic conditions (in either order). Complementary pharmaceutical modules can be paired with these environmental stages. When the system includes pairing a pharmaceutical agent to particular environmental conditions, the environmental adjustment and the pharmaceutical administration can be performed in either order or essentially simultaneously.

Any or all of the environmental control modules may also include a means for monitoring the environmental conditions using equipment known in the art. Providing real-time monitoring of the environmental conditions allows for adjustment of the conditions during circuit operation as necessary to optimize safety and efficacy. Aspects of the sequential opposite module concept are discussed in more detail below.

1. Temperature Control Module

Temperature elevation has been previously attempted both in vivo and in vitro circuits to directly kill pathogens by increasing the temperature (e.g., above 40° C.). This temperature modulation has not proved to be useful for in vivo treatment, as temperatures high enough to kill pathogenic organisms also kill human blood cells. In direct contradiction to previous attempts to kill pathogens, one embodiment of the temperature module in the disclosed extracorporeal system is modulated to increase the replication rate of the pathogens, which in turn renders them more susceptible to other means of attack (e.g., pharmaceutical, radiation, high hydrostatic pressure compression, and pulsed electrical field treatment modules).

Optimal blood culture growth rates for human blood pathogens vary anywhere from about 20° C. to about 40° C. Many pathogens thrive at temperatures of about 35° C. to about 40° C. Thus, in some embodiments, the temperature is increased to about 35° C. to about 40° C., about 37° C. to about 42° C., about 37° C. to about 40° C., about 37° C. to about 39° C., or about 38° C.

In other embodiments, the temperature is decreased to about 20° C. to about 35° C., about 20° C. to about 30° C., about 25° C. to about 35° C., or about 30° C. to about 36° C. MRSA, for example, often lives and rapidly grows on human skin that may be ten degrees or more lower than 37° C. Some *Listeria* bacteria actually grow best when incubated at close to 20° C.

In addition, temperature control modules may be used prior to or simultaneously with a treatment module, to provide the synchronized controlled cooling of the extracorporeal blood or blood fraction, which will be necessary in certain treatment modules. For example, the high hydrostatic pressure module, the pulsed electrical field treatment module, the sonification module, and the radiation module may cause some degree of fluid warming that is dependent upon the intensity and duration of the treatment utilized. Therefore, temperature module(s) may be used, for example, to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

2. Oxygen Control Module

Human blood cells are remarkably tolerant of dramatic changes in oxygen-concentration, and so the tolerable oxygen concentrations will be essentially unlimited. Nevertheless, preferred oxygen concentration ranges are provided for guidance. For anaerobic conditions, the oxygen concentration can be less than about 50, less than about 40, less than about 30, less than about 20, less than about 10, less than about 5, or less than about 1 mm Hg pressure. In one embodiment, the oxygen concentration is about 0.5 to about 40 mm Hg pressure. For aerobic conditions, the oxygen concentration can be about 50 to about 150, about 100 to about 150, or about 100 mm Hg pressure.

a) Increasing Oxygen

As discussed above, the environmental module of the disclosed system may include an oxygenation component. The oxygenation component can involve any method or device known in the art to increase the oxygen content of the blood. Exemplary oxygenation components include, but are not limited to, a micro-bubbler device, membrane diffusion devices, and devices as described in, e.g., U.S. Pat. No. 5,104,373.

Without being bound by a particular theory, it is believed that oxygen enrichment is advantageous for several reasons. First, increasing circuit oxygen levels will increase the replication rate for aerobic bacteria. This is significant because rapidly dividing cells are most susceptible to pharmaceuticals and radiation. Second, oxygen enrichment forces facultative anaerobic and anaerobic bacteria to utilize aerobic pathways of energy metabolism, thus allowing drugs that block aerobic metabolism to be more effective in attacking the bacteria's most efficient energy producing systems. This is important as multi-drug resistant pathogens (e.g., MRSA, *E. coli*), many other pathogenic bacteria, and many non-bacterial disease-causing microbes are facultative and can adapt to environments that are oxygen rich and oxygen poor. These facultative organisms are among the most threatening, as they are rapidly developing resistance to nearly all current antibiotic classes when used in traditional in vivo methods at the accepted concentrations. Additionally, raising oxygen levels decreases the resistance of MRSA to vancomycin, as well as restoring the effectiveness of aminoglycosides against resistant *E. coli*. In addition, certain drugs, including but not limited to carboxyquinolones (e.g., ciprofloxacin, levofloxacin, moxifloxacin), aminoglycosides, trimethoprim, and nitrofurantoin, have increased antimicrobial activity in high oxygen environments. Lastly, oxygen enrichment is useful to replace circuit oxygen that will naturally decrease due to metabolism by blood cells within the circuit.

b) Decreasing Oxygen

Oxygen may be removed by any method or device known in the art. In one embodiment, the "deoxygenating component" can be inherent to the system because oxygen concentration in the circuit will naturally decrease due to metabolism by blood cells. As needed, further reduction in oxygen can be accomplished by, e.g., a commercially available membrane diffusion device similar to those used to decrease blood oxygen for long term storage in blood banking operations.

Without being bound by theory, it is believed that oxygen deprivation is advantageous for several reasons. First, decreasing circuit oxygen levels will increase the replication rate for predominantly anaerobic pathogens. As explained above, this is significant because rapidly dividing cells are most susceptible to treatment and destruction by pharmaceuticals and radiation. Most pathogenic anaerobic bacteria will grow at levels of oxygen between about 1% to about 8%. Second, oxygen deprivation forces facultative anaerobic bacteria to utilize their default survival energy producing fermentation pathways that allow them to survive under conditions of severe environmental stress. This will allow attack with alternative antimicrobial drugs that are effective against the bacteria's anaerobic stress survival pathways such as metronidazole which uncouples anaerobic oxidative decarboxylation by acting as an electron sink and is rapidly lethal to anaerobes and facultative anaerobes alike. Furthermore, metronidazole has active metabolites that attack and destroy bacterial DNA. Industrial fermenting and water treatment operations have discovered natural plant and bacterial fermentation inhibiting chemicals, which may also be useful in this system.

Figure 14:
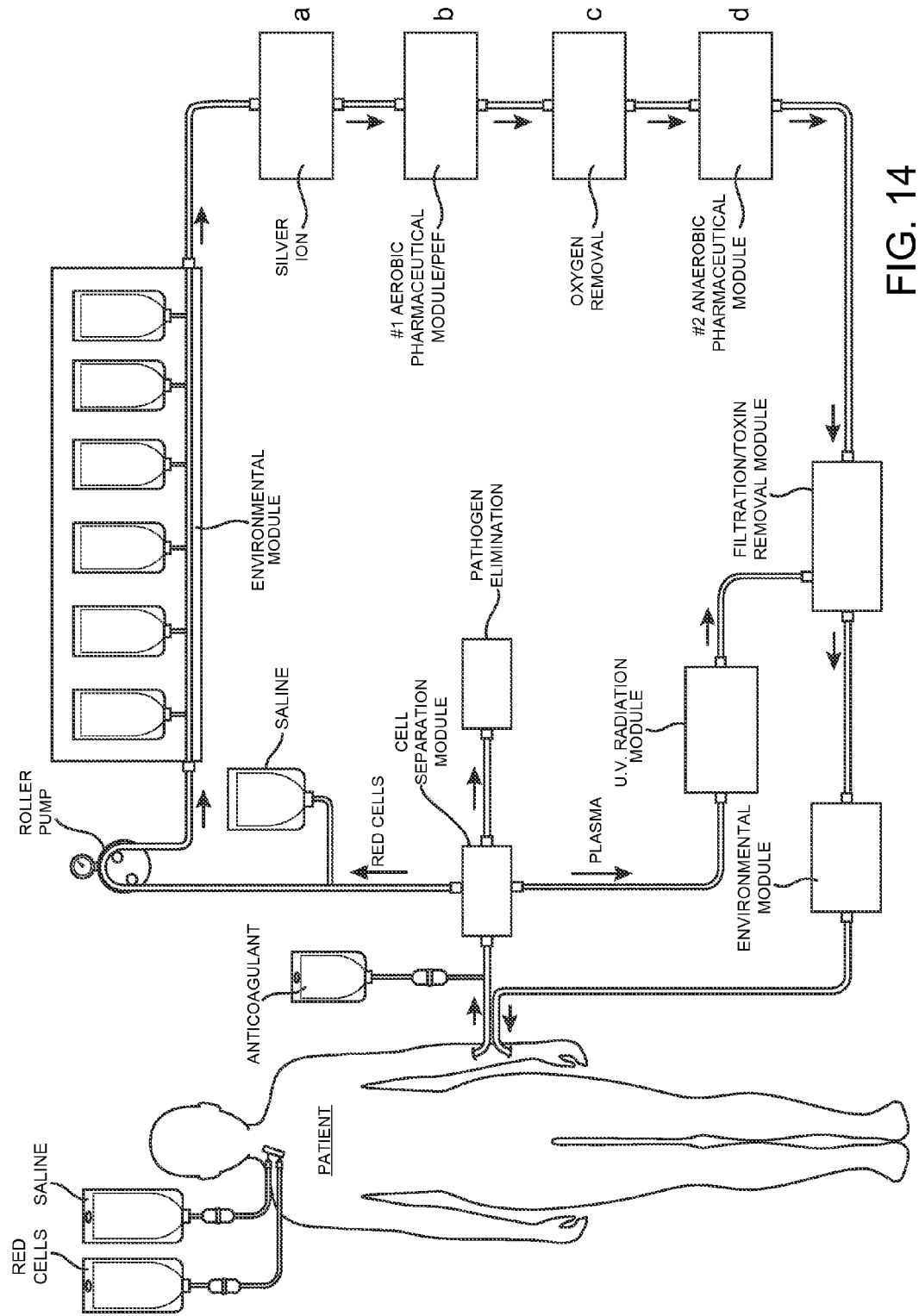
FIG. 14 is a schematic drawing that illustrates an exemplary embodiment of an extracorporeal system of the invention particularly designed for the treatment of MRSA. This embodiment includes an anticoagulant module, a separation module to separate the blood into a red blood cell fraction, a plasma fraction, and a buffy coat fraction comprising some of the pathogen (which is discarded and not returned to the patient). The red blood cell fraction is then subjected to a pretreatment environmental module and a pharmaceutical module for the delivery of silver ions to degrade bacterial capsule and membrane (shown as component a). The red blood cell fraction is also treated with a combination of a pharmaceutical module and a pulsed electric field (PEF) module under aerobic conditions (shown as component b) for treatment with a high dose of gentamicin and daptomycin, as well as a deoxygenation component using a low energy PEF to facilitate antibiotic penetration of the bacteria. The red blood cell fraction is treated with an oxygen removal module (shown as component c), and a combination of a pharmaceutical module designed for anaerobic conditions and a PEF module for treatment with a high dose of metronidazole and clindamycin using a low energy PEF to facilitate antibiotic penetration (shown as component d). The plasma fraction is subjected to UV radiation. Both the plasma fraction and the red blood cell fraction are filtered to remove pathogens and/or endotoxins, before proceeding to a post-treatment environmental module and returning to the patient.
Figure 16:
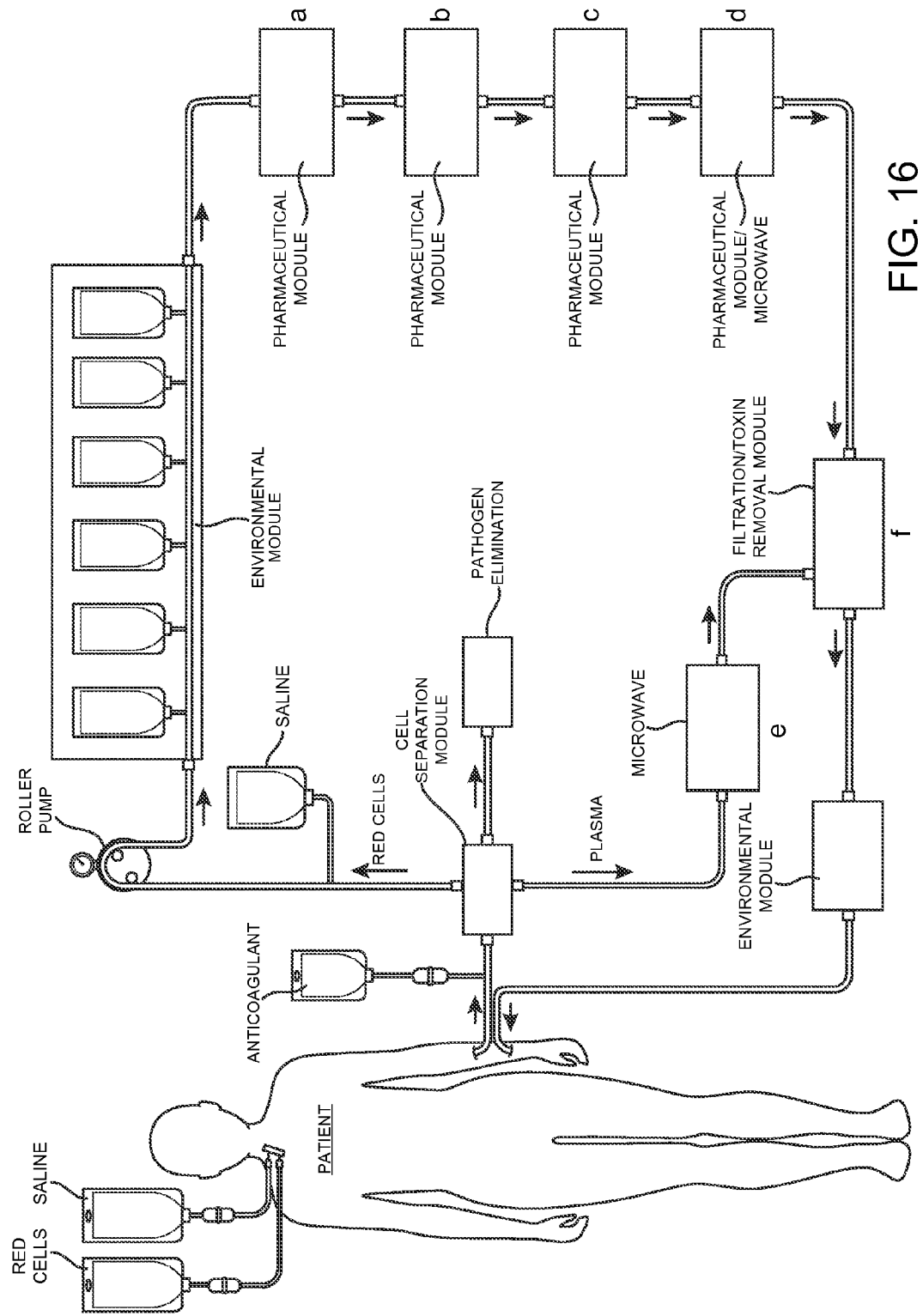
FIG. 16 is a schematic drawing that illustrates an exemplary embodiment of an extracorporeal system of the invention particularly designed for the treatment of malaria. This embodiment includes an anticoagulant module, a separation module to separate the blood into a red blood cell fraction, a plasma fraction, and a buffy coat fraction comprising some of the pathogen (which is discarded and not returned to the patient). The red blood cell fraction is then subjected to a pretreatment environmental module and a pharmaceutical module for the delivery of a high dose of quinine and clindamycin (shown as component a). The red blood cell fraction is also treated with another pharmaceutical module to deliver a high dose of artemether (shown as component b), as well as another pharmaceutical module to deliver a high dose of doxycycline (shown as component c). The red blood cell fraction is treated with a combination of a pharmaceutical module and a microwave module for treatment with a low energy microwave exposure to further reduce parasite viability (shown as component d). The plasma fraction is subjected to a microwave module with high energy microwave exposure to sterilize the plasma of any parasites (shown as component e). Both the plasma fraction and the red blood cell fraction are filtered to remove pathogens and/or parasite debris, before proceeding to a post-treatment environmental module and returning to the patient.
Figure 17:
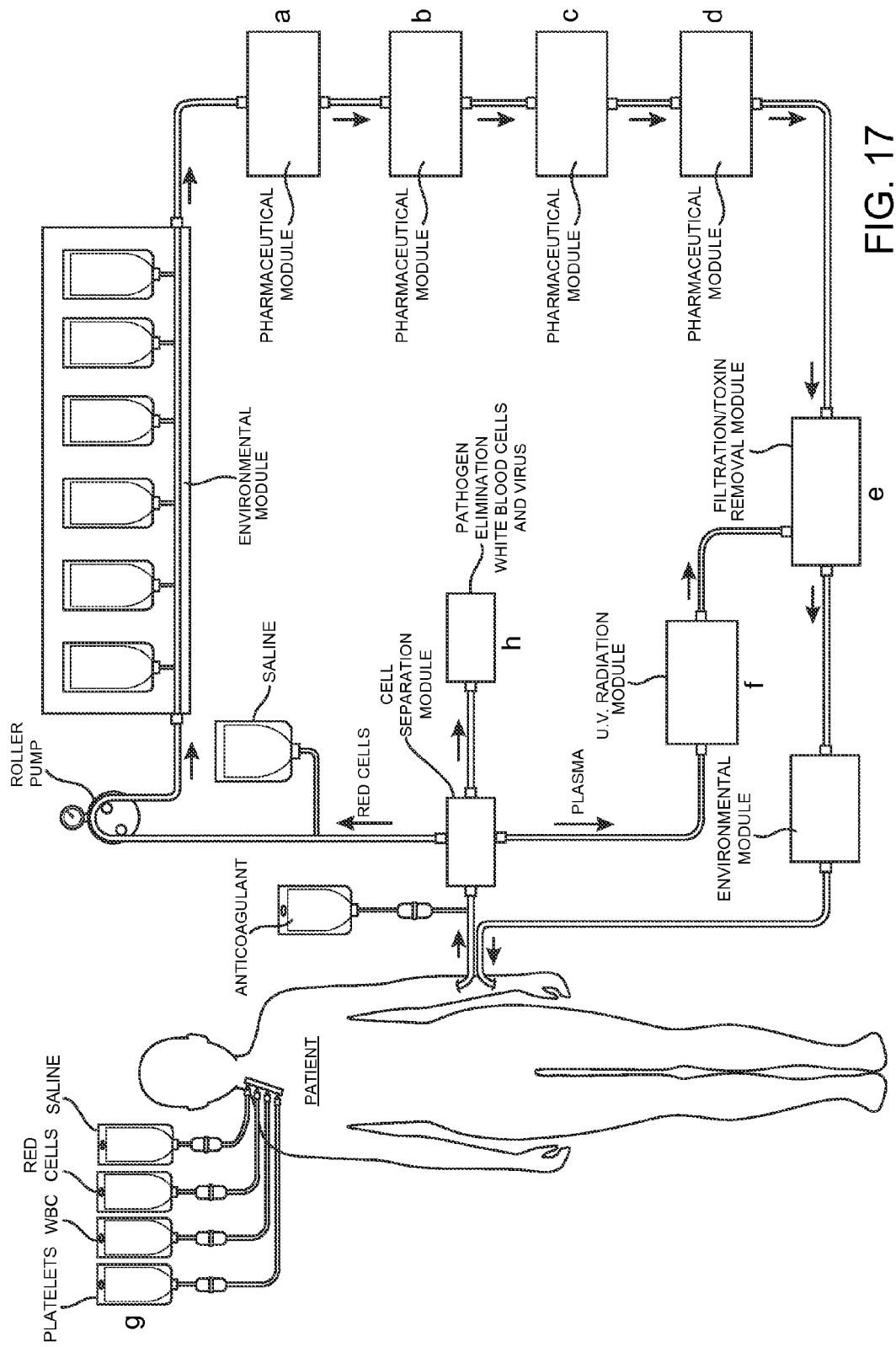
FIG. 17 is a schematic drawing that illustrates an exemplary embodiment of an extracorporeal system of the invention particularly designed for the treatment of hemorrhagic fevers such as Dengue and Ebola. This embodiment includes an anticoagulant module, a separation module to separate the blood into a red blood cell fraction, a plasma fraction, and a buffy coat fraction comprising some of the pathogen and infected white blood cells (which is discarded and not returned to the patient) (shown as component h). The red blood cell fraction is then subjected to a pretreatment environmental module and a pharmaceutical module for the delivery of an RNA-dependent polymerase inhibitor (shown as component a). The red blood cell fraction is also treated with another pharmaceutical module to deliver human recombinant interferon to degrade the virus (shown as component b), as well as another pharmaceutical module to deliver goat derived immunoglobulin specific to the hemorrhagic fever virus being treated (shown as step c). The red blood cell fraction is treated with a pharmaceutical module to deliver activated C-protein to augment the subject's natural anti-viral immune processes (shown as component d). The plasma fraction is subjected to a radiation module to deliver high energy UV radiation to sterilize plasma of the virus (shown as component f). Both the plasma fraction and the red blood cell fraction are subjected to a filtration module to remove specific viral endotoxins (shown as component e), before proceeding to a post-treatment environmental module and returning to the patient. In addition, platelets, white blood cells, red blood cells, and/or saline may be administered to the patient as a replacement to control hemorrhage and shock (shown as component g).

Sequential circuit exposures to alternating oxygen levels will allow for the pathogens to be controlled in a manner that both optimally increases their reproduction rate, as well as forcing them to utilize specific metabolic survival pathways that will then allow attack via specific antimicrobials that are most effective against anaerobic or aerobic metabolic pathways (See e.g., FIG. 14). The sequential circuit exposures can force the pathogen into less efficient metabolic pathways, permit attack of primary and secondary metabolic pathways independently, and overcome and/or evade the pathogen's evolutionary adaptive capabilities. Thus, the control methodology provides both new and effective techniques for combating bacterial hemosepsis and other blood pathogens.

3. pH Control Module

Controlling the pH of the blood provides the unique opportunity to modulate the pH to coordinate with the pKa of the pharmaceutical agent to be administered. Without being bound by theory, it is believed that modulating pH according to the drug's pKa (i.e., coordinating the pH module and the treatment module) helps the drug to penetrate the pathogen membranes (e.g., bacterial cell walls) and enter the cytoplasm. Once inside, the drugs are re-ionized and trapped inside the pathogen, where they will continue to drive the concentration gradient to promote further antimicrobial diffusion into the pathogen. For acidic drugs, the pH of the blood or blood fraction should be decreased. Examples of acidic drugs include, but are not limited to, finafloxacin, delafloxacin, beta-lactams (e.g., oxacillin), fusidic acid, and rifampicin. For basic drugs, the pH of the blood or blood fraction should be increased. One non-limiting example of a basic drug is vancomycin which is capable of killing *S. aureus* under basic conditions better than under slightly acidic conditions. Complete deionization is not required; simply increasing the deionization will increase permeability, and thus efficacy. Table 1 provides a list of exemplary drugs and their respective pKa values, which would inform the appropriate pH conditions. This list is not intended to be limiting, and the pKa value for any drug is readily available (see, e.g., the United States Pharmacopeia (USP)) and/or ascertainable.

TABLE 1

| Drug | pKa |
|---|---|
| Amikacin | 12.7 |
| Amoxicillin | 2.4 |
| Amphotericin | 2.5 |
| Azithromycin | 8.1 |
| Aztreonam | 0.5 |
|  | 2.6 |
|  | 3.7 |
| Ceftazidime | 1.8 |
|  | 2.7 |
|  | 4.1 |

TABLE 1-continued

| Drug | pKa |
|---|---|
| Ceftriaxone sodium (COOH) | 3 |
| (NH$_2$) | 3.2 |
| Cefotaxime sodium | 3.8 |
| Cefoxitin sodium | 2.2 |
| Cefuroxime sodium | 2.5 |
| Cephalexin | 3.2 |
| Ciprofloxalin | 6.1 |
|  | 8.6 |
| Clindamycin | 7.5 |
| Colistin | 12.1 |
| Colistimethate | 3.9 |
| Daptomycin | 5.3 |
| Asp-3 | 4.2 |
| Asp-7 | 1.5 |
| Asp-9 | 3.8 |
| mGlu-12 | 4.6 |
| Kyn-13 | 1.3 |
| Gentamycin | 8.2 |
|  | 13.2 |
| Imipenem | 3.2 |
|  | 9.9 |
| Levofloxacin (carboxylic group) | 5.5 |
| (piperazinyl group) | 8 |
|  | 6.8 |
| Linezolid | 5.0 |
|  | 1.7 |
| Lincomycin | 7.5 |
| Metronidazole | 2.5 |
| Methicillin | 3.0 |
| Minecycline | 7.8 |
| Naladixic acid | 6 |
| Norfloxacin | 6.3 |
|  | 8.8 |
| Penicillin G | 2.8 |
| Polymixin | 8.9 |
| Polymixin B sulfate | 12.0 |
| Quinine | 8.1 |
| Rifampicin (-hydroxy) | 1.7 |
| (3-piperazine nitrogen) | 7.9 |
| Sulfoxazole | 5.0 |
| Ticarcillin | 3.0 |
| Tigecycline | 4.4 |
| Tobramycin | 6.7 |
|  | 8.3 |
|  | 9.9 |
| Trimethoprim | 6.6 |
| Trovafloxacin (COOH) | 5.9 |
| (NH$_2$) | 8.1 |

The opportunity to modulate pH is uniquely possible in an extracorporeal system or method of the invention, where the pH of the blood or blood fraction can be modified to, e.g., pH values between about 4.5 to about 9. In contrast, changing the pH in vivo is not feasible because human blood pH is tightly regulated at a pH of about 7.4, and significant deviations from this value are not tolerated. Similarly, although some prior art has suggested imposing dramatic changes to blood pH ex vivo to kill pathogens directly, such methods have proved ineffectual and/or detrimental to blood cells, other critical tissues, and essential human enzyme functions.

The pH of the blood or blood fraction can be decreased by any physiologically acceptable acidic compound including, but not limited to, carbonic acid, ammonium chloride, citric acid, hydrochloric acid, lactic acid, acetic acid, and pyruvic acid. Conversely, the pH can be increased by any physiologically acceptable basic compound such as bicarbonate or a stronger base. Just as high concentrations of pharmaceutical agents will be tolerated extracorporeally as explained in further detail below, high concentrations of pH adjusters will be similarly tolerated ex vivo.

In some embodiments, modifying the pH can restore efficacy to previously approved, but now ineffectual drugs in the antibiotic arsenal. For example, aminoglycoside antibiotics now fail to kill resistant strains of E. coli under low pH conditions. Both the influx of the antibiotic into the bacterial cytoplasm and the ribosomal binding of the aminoglycoside are impaired at low pH conditions. The extracorporeal system can couple increased pH with aminoglycoside antibiotics (and moreover, the antibiotics can be administered at concentrations higher than those acceptable in vivo as explained below). Further discussion of drugs that may be useful in the disclosed extracorporeal system is provided below.

Also, modulating pH (particularly decreasing pH) can also serve as another form of environmental stress that can be inflicted on the pathogenic organism. A pathogen can be subjected to a combination of conditions rarely, if ever, seen in vivo, conditions under which the pathogen is evolutionarily ill-equipped. For example, a common hemosepsis environment in vivo is often characterized by low pH, high partial pressure of oxygen, and high glucose. By changing one or more of these variables in the disclosed extracorporeal system, the pathogen is exposed to unnatural, unfamiliar conditions that facilitate the reduction and/or elimination of the pathogen.

4. Nutrient Control Module

Pathogens are sensitive to the levels of carbohydrates (e.g., glucose), amino acids (e.g., tryptophan), iron, other trace elements, and other key nutrients in their environments. By default, many pathogens use glucose as a primary substrate for metabolism. In particular, during sepsis, blood glucose is often higher than normal and so is readily available. By manipulating the nutrient environment of the blood or blood fraction, one can direct the pathogen toward non-glucose metabolic pathways, which are often also anaerobic pathways (i.e., fermentation pathways). Additionally, it will be desirable to substitute other non-glucose sugars such as lactose, pentose sugars, mannitol, and other energy substrates in order to expose alternative microbial metabolic pathways to attack. Forcing bacteria to use their alternate survival metabolic pathways invites the use of different antimicrobial agents (e.g., fermentation-blocking compounds) that attack these alternative metabolic pathways. In some embodiments, the glucose levels will be about 0.01 to about 300, 0.01 to about 5, about 5 to about 10, about 10 to about 20, about 20 to about 40, about 40 to about 100, or about 100 to about 300 mg/dL.

a) Increasing Nutrients

Increasing nutrients, e.g., glucose and iron concentrations can increase the replication rate, thus increasing susceptibility to pharmaceutical agents and radiation as discussed above. Paradoxically, some microorganisms will switch to fermentation-based energy production when placed in a high glucose environment even in the presence of oxygen.

b) Decreasing Nutrients

Significantly lowering glucose in vivo is lethal to human beings, but not to blood cells. Thus, decreasing glucose is an environmental condition exclusively available in an extracorporeal system. When stressed by a low glucose environment, resistant pathogens must activate alternative non-glucose utilizing pathways to make energy, albeit less efficiently. This involves synthesizing new enzymes to drive the low glucose survival energy pathways.

The extracorporeal systems and methods of the invention may include directing the pathogens toward such alternative metabolic pathways, and while under such alternative metabolic conditions, administering protein synthesis inhibiting drugs to target the pathogens in this vulnerable state. Multiple potential anti-metabolic drugs exist that can interfere with many aspects of microbial metabolism, but they are not effective against resistant pathogens under normal or elevated blood glucose conditions. Thus, the extracorporeal systems and methods of the invention provide a unique opportunity to use current anti-metabolic drugs such as sulfoxazole, trimethoprim, various chemotherapeutic medicines, anti-fermentation agents, protein synthesis inhibiting drugs, as well as drugs not otherwise available for treatments.

5. Carbon Dioxide Control Module

The carbon dioxide module may be included in the disclosed extracorporeal system as an environmental module and/or as a treatment module. Carbon dioxide ($CO_2$) is a non-toxic gas with antimicrobial properties. Desirably, $CO_2$ can be easily added and removed by manipulating the pressure and temperature of a solution. The antimicrobial effectiveness of $CO_2$ depends on the pressure and temperature, but is also affected by the state of $CO_2$ (i.e., gas, liquid or supercritical fluid (SCF)) and the concentration of dissolved $CO_2$. The SCF region for $CO_2$ is above the critical temperature of 31° C. (Tc) and critical pressure of 7.4 MPa (Pc). SC $CO_2$ has properties between liquid and gas with higher dissolving and penetrating powers that facilitate entry through cell walls and into spores where $CO_2$ could lower the pH or even extract the contents of microbial cell. The antimicrobial action is primarily due to oxidation of the outer cell membranes of vegetative bacteria, endospores, yeast, and molds.

$CO_2$ may be added to the blood or blood fraction by any methods known to one of ordinary skill in the art. For example, in some embodiments, the $CO_2$ is added to solution by: a) bubbling $CO_2$ in a vessel at low temperature and at slightly elevated pressures; b) adding $CO_2$ to the headspace of a compressible container and then exposing to high pressure; and c) using $CO_2$ as the pressuring medium by injecting into a vessel at high pressure. A variation of this technique is bubbling $CO_2$ through a microfilter producing microbubbles that stay suspended in the solution.

In certain embodiments, the carbon dioxide module is used as an environmental module in conjunction with a treatment module. For example, microbial inactivation by high pressure (HHP), discussed below, increases with adding $CO_2$, increasing temperature, pressure, and/or time. Accordingly, in certain embodiments, the carbon dioxide module is used sequentially or simultaneously with an HHP module to maximize the antimicrobial effect.

In other embodiments, the carbon dioxide module is used in this extracorporeal system as a treatment module. $CO_2$ can be easily added and removed by manipulating the pressure and temperature of a solution. The solubility of $CO_2$ in water is expressed in volumes of dissolved $CO_2$ per unit volume of water, and the solubility increases with pressure and decreases with temperature. In one embodiment, $CO_2$ enhanced the inactivation of Listeria when added at a carbonation volume of about 2 at about 35° C., and pressure of up to about 350 MPa for about 300 seconds.

6. Osmolality Module

In certain embodiments, the disclosed modular extracorporeal system may include a module that affects the osmolality of the fluid. The osmolality of any given blood sample may be different, depending on the particular health condition of the subject. In certain embodiments, the osmolality may be modified with the use of a hypertonic solution and distilled water.

In certain embodiments, the osmolality module is used as an environmental module in conjunction with a treatment module. For example, in certain embodiments, the osmolality module is used sequentially or simultaneously with an HHP module or a PEF module in order to maximize the antimicrobial effect. Similarly, the osmolality module may be used after any treatment in order to restore the fluid to a condition suitable for transfer back to the patient.

E. Treatment Module

The disclosed modular extracorporeal system can include one or more treatment modules which may include a pharmaceutical module, a radiation module, a hydrostatic compression module, a cell/pathogen separation module as described above, a pulsed electrical field module, a microwave module, and/or a sonification module (see, e.g., FIGS. 4-9).

1. Pharmaceutical Module

Figure 4:
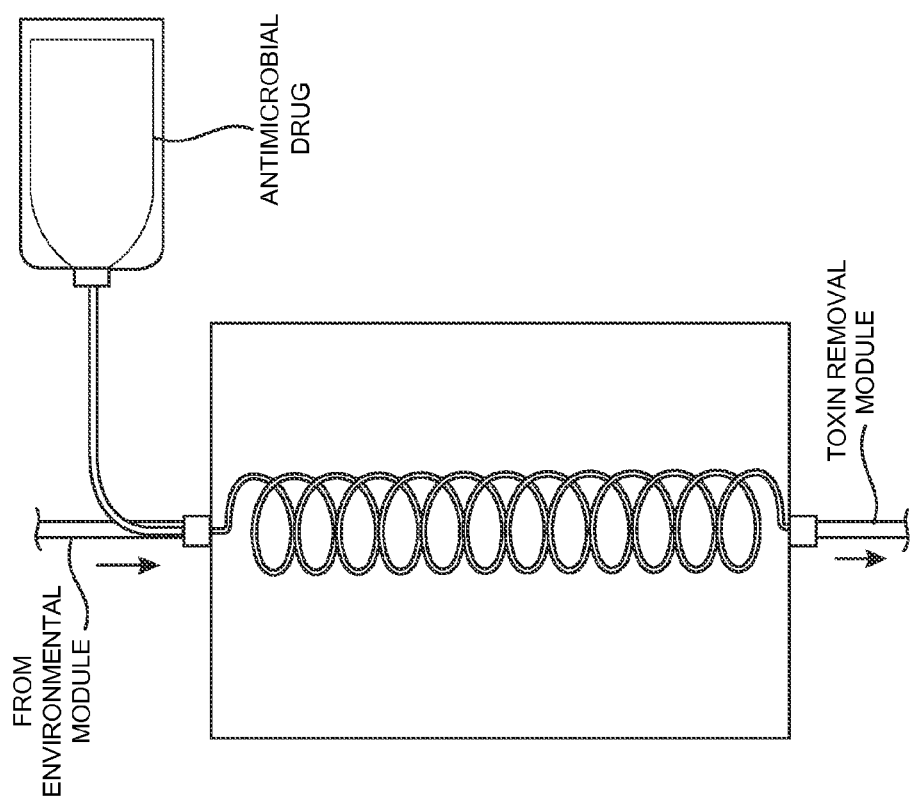

The modular extracorporeal system can include one or more pharmaceutical modules (see, e.g., FIG. 4). Each pharmaceutical module may be paired with the particular environmental conditions at that point in the extracorporeal system of the invention. Because in vivo toxicity is not applicable to the extracorporeal system, drugs may be administered at high concentrations, even concentration higher than those tolerated in vivo. For example, linezolid is a promising, relatively new antibiotic effective against resistant bacteria, but toxic side effects have limited its use. But in an extracorporeal system, linezolid and other drugs may be used without causing toxic side effect. Also, the system of the invention allows for the use of agents that have no tolerable in vivo dose. In other words, drugs that are effective to kill pathogens but are simply too lethal to use in vivo may now be employed extracorporeally. Such toxic drugs include historically toxic substances such as arsenic as well as drug candidates that have failed or will fail in clinical trials. Table 2 provides a non-limiting list of certain examples of drugs that have toxic effects or limitations when used in vivo, but that would be suitable for use in the disclosed extracorporeal system.

TABLE 2

| Drug | Spectrum, activity | Issues with Respect to In vivo Toxicity or Side Effects |
| --- | --- | --- |
| Amikacin | Gram negative, bactericidal | Nephrotoxicity, ototoxicity |
| Gentamicin | Gram negative, bactericidal | Nephrotoxicity, ototoxicity |
| Tobramicin | Gram negative, bactericidal | Nephrotoxicity, ototoxicity |
| Trovafloxacin | Broad, bactericidal | Histamine release, Idiosyncratic reactions |
| Moxifloxacin | Broad, bactericidal | Increase in dose limited due to tolerability issues QT interval prolongation |
| Levofloxacin | Broad, bactericidal | Increase in dose limited due to tolerability issues |
| Ciprofloxacin | Gram negative, bactericidal | Increase in dose limited due to tolerability issues |
| Daptomycin | Gram positive, bactericidal | Increase in dose limited due to toxicity |
| Colistin, Polymixin B | Gram negative, bactericidal G−, bactericidal | Only used as last resort antibiotics due to renal and neurotoxicity |
| Tigecycline | Broad, static | Increase in dose limited due to GI tolerability issues |
| Minocycline | Broad, static | Increase in dose limited due to GI tolerability issues |

Also, a drug in vivo is metabolized and/or quickly diffuses out of the bloodstream, neither of which is applicable ex vivo. Accordingly, drugs may be administered at lower doses extracorporeally since the entire drug dose will remain in the blood or blood fraction.

A simplified example of the extracorporeal pharmaceutical module"s "high in vitro concentration/low in vivo concentration" is as follows: A dose of an antimicrobial drug is 1 gram metered into a 1 liter pharmaceutical module, which produces a high drug concentration of 1 mg per ml. If the volume of distribution for this drug is 100 liters, then the concentration in the human body would only be 0.01 mg/cc without even accounting for in vivo metabolic deactivation of the drug and/or its clearance from the body via the hepatic and renal systems. In effect, the total dose of the antimicrobial washing back into the patient after transit through the high concentration pharmaceutical module may be so minimal, that in many situations the patient will need to be administered some additional parenteral antimicrobial drug simply to attain the appropriate minimum inhibitory concentration.

Appropriate initial ex vivo doses can be calculated by one of ordinary skill in the art of pharmacokinetics based on the minimum inhibitory (MIC, $IC_{50}$), minimum effective ($EC_{50}$), and/or median lethal dose ($LD_{50}$) for any particular drug. Doses will also take into consideration the extracorporeal blood volume (e.g., about 0.5 to about 2 L), duration of the circuit, and age, gender, weight, and condition of the subject.

Exemplary pharmaceutical agents include, but are not limited to, antimicrobial, anti-viral, antibiotic, anti-fungal, and anti-parasitic drugs. Specific exemplary pharmaceutical agents include, but are not limited to, beta-lactams, sulfonamides, quinalones, aminoglycosides, carboxyquinolones (e.g., ciprofloxacin, levofloxacin, moxifloxacin), protein synthesis inhibitors, vancomycin and related drugs (e.g., teicoplanin), ketolides, quinupristin and/or dalfopristin, linezolid, bacteriocins, mupirocin, anti-neoplastics, daptomycin, anti-glycolytics, gluconeogenesis inhibitors, anti-metabolites (e.g., folate, pyrimidine, cytidine, purine), detergents (e.g., polymixin B, colistin), transitional metals, heavy metals, cycloserine, anti-fungals (e.g., amphotericin B, fluocytosine, imidazoles, triazoles, echinocandins), fermentation inhibitors, anti-herpes virus agents (e.g., acyclovir family), anti-influenza agents (e.g., amantadine family, oseltamvir, zanamivir), anti-hepatitis agents (e.g., adefovir, interferon-alfa, lamivudine, pegylated interferon), ribavirin, imiquimod, cidofovir, anti-retroviral agents, protease inhibitors, anti-malarials (e.g., quinine family, artemisinin family, atovaquone), eflornithine, melarsoprol, nitroimidazoles, pentamidine, sodium stibogluconate, other ancient antimicrobial agents to include heavy metal compounds, suramin, and benzimidazoles.

In some embodiments, more than one drug can be administered via a single pharmaceutical module.

In some embodiments, multiple pharmaceutical modules are sequentially employed to subject the pathogen to an orchestrated attack. For example, a first pharmaceutical module can employ agents that attack cell walls, membranes, or capsules. Gram positive bacteria such as MRSA possess thick cell wall capsules, which impede their uptake of drugs. Drugs such as ionized silver can degrade microbial cell walls and/or cell membranes. A pulsed electrical field module also may be used to increase bacterial pore size and allow antimicrobial agents to more easily enter the pathogen's cytoplasm. Drugs such as daptomycin and vancomycin can be employed to further attack the cell membranes and/or cell wall capsule. After this exposure, the a second pharmaceutical module can be employ drugs such as azithromycin or linezolid that will now more easily gain access to the cytoplasm of the pathogen and attack critical microbial metabolic pathways for energy metabolism, protein synthesis, and reproduction.

In another embodiment, pharmaceutical modules are sequentially or simultaneously paired with environmental control modules. For example, modules effecting aerobic conditions can be paired with pharmaceutical agents effective in aerobic conditions. Additionally or alternatively, modules effecting anaerobic conditions can be paired with pharmaceutical agents effective in anaerobic conditions. Exemplary pharmaceutical agents effective in anaerobic conditions include, but are not limited to, metronidazole and clindamycin. Exemplary pharmaceutical agents effective in aerobic conditions include, but are not limited to daptomycin, beta-lactams, erythromycins, trimethoprim, and nitrofurantoin. Some drugs, such as ionic silver, can be effective in either aerobic or anaerobic conditions (see, e.g., FIG. 14).

In another example of this embodiment in which a pharmaceutical module is paired with an environmental control module, the environmental module causes a decrease in the pH of the blood or blood fraction in order to make the pharmaceutical agent more effective against the pathogen. For example, the pH may be decreased, and a quinolone, aminoglycoside, or beta-lactam may be used. Both finafloxacin (8-cyano subclass) and delafloxacin (which are in clinical development) show an increase in activity at an acidic pH. Finafloxacin exhibits a 4- to 8-fold increase in activity (denoted by a 4- to 8-fold lowering of the MIC) at pH 6.0 compared to activity at pH 7.4. A similar effect is observed with delafloxacin. These changes in activity are likely to be a result, at least in part, of a transmembrane diffusion model, in which uncharged (neutral or zwitterionic) species cross the membranes more easily than those having a net charge. At acidic pH, 50% of delafloxacin is under a neutral form, favoring its uptake over other agents.

In addition to small molecule pharmaceutical agents, other agents such as bacteriocins can be used in the pharmaceutical module(s). Bacteriocins are small, heat stable proteins that are produced by nonpathogenic bacteria that attack disease causing bacteria. Their spectrum of coverage is narrow, but the progress of rapid DNA-based bacterial identification will allow precise utilization of these narrow spectrum antimicrobial compounds. For example, the bacteriocin lysostaphin can be employed in an extracorporeal pharmaceutical module to attack MRSA.

In one embodiment, the pharmaceutical agent is concentration dependent. This means that the higher its concentration, the more quickly and thoroughly it kills or impairs the pathogens. The system's ability to safely produce and expose pathogens to super high concentrations of such antibiotics will be maximized.

Suitable drugs include both bacteriocidal and bacteriostatic drugs. In some embodiments, at least one bacteriocidal drug is administered. In one embodiment, a bacteriostatic drug is administered, and another mode of attack, e.g., bacteriocidal agent or radiation, is also employed.

The extracorporeal system of the invention can optionally include a module that removes all or some of the pharmaceutical agent before blood return. This toxin removal module (see, e.g., FIG. 1) and described further below can reduce the pharmaceutical agent concentration to a tolerable in vivo dose. Alternatively, such a module can remove substantially all of the pharmaceutical agent before blood return, which may be useful for agents that do not have a tolerable in vivo dose.

In one embodiment, the pharmaceutical agent is silver. Without being bound by theory, the silver ion reacts with sulfhydryl or thiol groups and has negative effects on microbial enzymes, proteins, cell walls, and cell membranes. Silver is a transitional metal as opposed to heavy metals such as lead, and therefore has less toxicity in humans, as it preferentially destroys microbial cells. In one embodiment, the pharmaceutical module administers ionic silver, e.g., at concentrations of about 0.01 to about 0.5 ppm, about 0.05 to about 4 ppm, about 0.1 ppm to about 0.3 ppm, or about 0.2 ppm. In this embodiment, the silver can be introduced into the blood as silver chloride solution or via a simple electrolytic donor plate device.

2. Radiation Module

Figure 5:
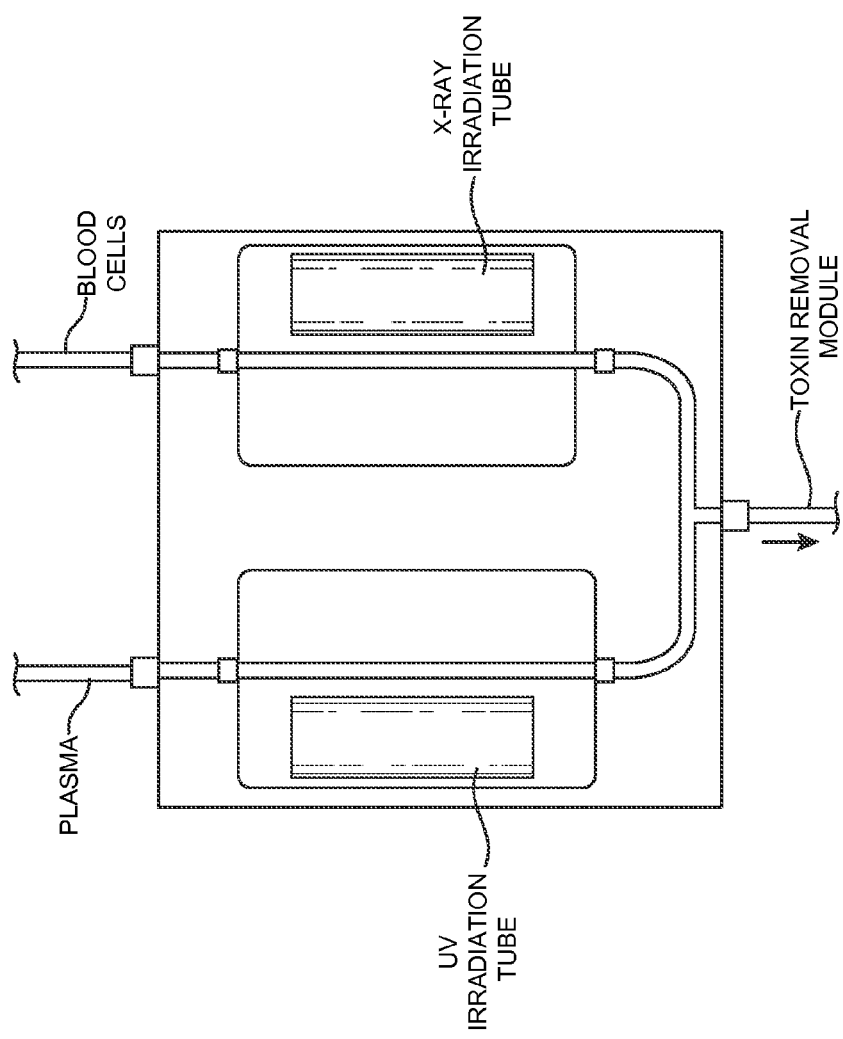

In some embodiments, the extracorporeal system of the invention may include one or more radiation modules (FIG. 5). The radiation module can deliver X-ray, ultraviolet (UV), light emitting diode (LED), infrared (IR) (with and without riboflavin other potentiators), and visible, laser, and/or radiofrequency radiation. In one embodiment, the radiation module delivers X-ray and/or UV radiation. Like the pharmaceutical modules, multiple types or strengths of radiation may be delivered via a single radiation module (See, e.g., FIG. 5), or multiple radiation modules may be incorporated into the extracorporeal system.

Without being bound by theory, it is believed that radiation degrades cell walls, thus potentially rendering the pathogens more susceptible to pharmaceutical attack. Radiation also inhibits lymphocyte cytokine release, which will decrease cytokine-mediated shock in subjects.

In one embodiment, the blood (or blood fraction(s)) are subjected to about 1 to about 500, about 5 to about 150, about 25 to about 100, or about 50 to about 75 gray units of X-ray radiation.

As noted above, UV radiation inherently generates variable amounts of heat, depending on the particular parameters used. Therefore, the UV radiation module in some embodiments, is sequentially or simultaneously coupled with an environmental module that decreases the temperature of the blood or blood fraction. In certain embodiments, the temperature module is used to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

3. Hydrostatic Compression Module

In certain embodiments, the extracorporeal system of the invention may include one or more hydrostatic compression (high hydrostatic pressure (HHP)) modules (FIG. 6). An HHP module will consist of a special circuit or vessel that can be hermetically sealed and then pressurized via a fluid pump capable of producing elevated extracorporeal pressure to achieve microbial inactivation. In certain embodiments, the pressure ranges from about 50 MPa to about 1,100 MPa, about 50 MPa to about 1,000 MPa, about 100 MPa to about 1,000 MPa, about 100 MPa to about 400 MPa, or about 400 MPa to about 1,000 MPa. The pressure may be applied as a single continuous treatment, or as a series of sequential cycles.

In certain embodiments, HHP modules are sequentially or simultaneously paired with environmental control modules and/or other treatment modules. For example, the temperature may be modulated higher or lower prior to, during, and immediately after HPP treatments, in order to maximize antimicrobial effects and to avoid overheating of the extracorporeal fluids. In addition, pH modulation may also be utilized with the HHP module as titration of pH can positively impact HHP microbial inactivation.

A pharmaceutical module also may be included prior to, during, or after pressurization with HHP, as a pharmaceutical agent can have synergistic antimicrobial effects when combined with increased fluid pressures. In addition, in certain embodiments, carbon dioxide is added to the fluids in the HHP module as the presence of carbon dioxide dramatically enhances the antimicrobial effects of HHP treatments when added to the fluid being treated at or near its supercritical fluid phase (which can be created in the module via modulation of temperature and pressure). Under these conditions, carbon dioxide can penetrate both bacterial cell walls, as well as thick spore capsules, where it can abruptly decrease intracellular pH and then, upon depressurization, extract the contents of the microbial cell. In some embodiments, the $pCO_2$ levels used in the HHP module range from about 45 to about 200 mm Hg, about 45 to about 175 mm Hg, or about 75 to about 150 mm Hg. In certain embodiments, the $pCO_2$ levels used in the HHP module range from about 45 to about 150 mm Hg.

As noted above, HHP inherently generates variable amounts of heat, depending on the particular parameters used. Therefore, the HHP module in some embodiments, is sequentially or simultaneously coupled with an environmental module that decreases the temperature of the blood or blood fraction. In certain embodiments, the temperature module is used to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

HHP has variable effects at various pressurization levels. Pressurization levels below 400 MPa can cause changes to cellular morphology and function that are reversible with depressurization. Once cellular pressures exceed 400 MPa, the effects are irreversible, and include separation of the cell wall from cell membrane, loss of osmotic responsiveness, enzymatically driven DNA shearing, and loss of protein, RNA, and metal ions to the extracellular fluid.

4. Pulsed Electric Field Module

In certain embodiments, the extracorporeal system of the invention may include one or more pulsed electric field (PEF) modules (FIG. 7). PEF treatment utilizes the application of high voltage pulses to manipulate the cell membrane of a pathogen. In certain embodiments, the high voltage pulse ranges from about 10 to about 100 kV/cm, about 10 to about 80 kV/cm, about 20 to about 100 kV/cm, or about 20 to about 80 kV/cm. In certain embodiments, the electrical pulse is applied for about 0.5 to about 600 microseconds, about 0.5 to about 500 microseconds, about 1 to about 600 microseconds, or about 1 to about 500 microseconds. The electrical pulse may be applied to a static or circulating fluid flowing in parallel, co-axial, or co-linear configurations within the module. In certain embodiments, the fluid can be treated by the PEF module in a stepwise circulation mode or a recirculation mode.

The PEF module is particularly suitable to the treatment of yeast and gram negative bacterial pathogens, although it is useful under for the treatment of other pathogens as well. PEF mainly targets microbial cell membranes, and its effects are reversible at lower levels of exposure. PEF causes disruption to the morphology and functional integrity of the cell membranes and their pores. At lower levels of energy, changes in the microbial cell membranes are transient and reversible, whereas higher levels of energy will cause cell rupture or electroporation. Because the effectiveness of PEF depends upon pH, presence of antimicrobial and ionic compounds, solution conductivity, ionic strength, and growth phase of the microbes, in certain embodiments, the PEF module is sequentially or simultaneously coupled to one or more environmental or other treatment modules (e.g., pharmaceutical module) to be most effective against pathogens. In one embodiment, lower levels of PEF are applied and have the potential to facilitate delivery of many antimicrobial agents, including ancient heavy metals into the cytoplasm of microbes, while defeating microbial resistance mechanisms such as efflux pumping. Although spores are relatively resistant to PEF, multiple sequential and/or simultaneous physical and chemical attacks within the extracorporeal circuit should prove effective in degrading hardy spores.

As noted above, PEF inherently generates variable amounts of heat, depending on the particular parameters used. Therefore, temperature modulation may be necessary for PEF, both to adjust the growth phase of microbes prior to initiation of treatments, and to cool the extracorporeal fluids during and after treatments. Accordingly, the PEF module in some embodiments, is sequentially or simultaneously coupled with an environmental module that decreases the temperature of the blood or blood fraction. In certain embodiments, the temperature module is used to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

5. Microwave Module

In certain embodiments, the extracorporeal system of the invention may include one or more microwave modules (FIG. 8). This module is particularly suitable for the treatment of malarial pathogens in the blood or blood fraction. *Plasmodium* species parasitize red blood cells, and the parasitized cells adhere to vessel walls, causing stasis and inflammation (e.g., causing cerebral malaria when it occurs in the brain vasculature). Malarial parasites within red blood cells concentrate and detoxify iron from hemoglobin molecules in a form ($Fe^{+++}$) that renders the iron deposits susceptible to heating by microwave. The heat of the microwave destroys both the parasite and the red blood cell. In certain embodiments, the microwave module is used at about 0.5 to about 25 cm, about 0.5 to about 20 cm, about 1 to about 25, or about 1 to about 20 cm wavelengths. In certain embodiments, the microwave module uses an energy level of about 0.5 to about 20 W. In certain embodiments, the energy level is about 1 to about 100 mW, or about 100 to about 200 mW. In some embodiments, the microwave module treats the fluid for about 50 microseconds to about 15 seconds, about 50 microseconds to about 10 seconds, about 100 microseconds to about 15 seconds, or about 100 microseconds to about 10 seconds.

The selectively destroyed red blood cells (i.e., parasitized cells) and/or their contents (e.g., excess liberated iron) can then be removed by various treatments, including those discussed above or below, such as filtration, centrifugation, chelation, adhesion, or microfluidic separation techniques. Additional measures to remove free hemoglobin from the blood or blood fraction may be necessary, depending on the level.

Microwave inherently generates variable amounts of heat, depending on the particular parameters used. Therefore, temperature modulation may be necessary for the microwave module to cool the extracorporeal fluids during and after treatments. Accordingly, the microwave module in some embodiments, is sequentially or simultaneously coupled with an environmental module that decreases the temperature of the blood or blood fraction. In certain embodiments, the temperature module is used to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

6. Sonification Module

In certain embodiments, the extracorporeal system of the invention may include one or more sonification modules (FIG. 9). Ultrasound is the energy generated by sound waves of frequencies above the human hearing and is roughly defined by a frequency range from about 10 kHz to about 1.5 GHz, about 10 kHz to about 1 GHz, about 18 kHz to about 1.2 GHz, or preferably about 18 kHz up to about 1 GHz. Ultrasonic waves are created by magnetostrictive or piezoelectric transducers, which transform electrical energy into mechanical oscillations, and are transferred into the treatment medium either directly via sonotrodes or indirectly in case of ultrasonic baths. The longitudinal sound waves can be transmitted into fluids causing cyclic compressions and rarefactions of the material. High-intensity, low-frequency (about 10 to about 150 kHz, about 16 to about 150 kHz, about 10 to about 100 kHz, or about 16 to about 100 kHz) ultrasound can lead to cavitation, the creation, growth, and violent collapse of gas bubbles. The bubble collapse is accompanied by high pressure and temperature peaks (up to about 100 MPa and about 5000 K) as well as intense local shear. Such high power ultrasound treatments have the potential to improve mass transfer processes and heat transfer. In contrast, low intensities and high frequencies in the MHz-range lead to sonication treatments with acoustic streaming as the main mechanism. Such low energy ultrasound is used for non-destructive testing as well as for the stimulation of living cells.

Cavitation and associated phenomena can reduce the use of chemicals needed for antimicrobial treatment. With respect to microorganism inactivation, the singular use of ultrasound is generally rated insufficient, but ultrasound is promising in combination with other treatments because sonication induced cell damage leads to a higher sensitivity towards other treatments. Therefore, in the disclosed systems and methods, when a sonification module is included, typically one or more additional treatment modules are included to maximize the antimicrobial effect.

As noted above, sonification inherently generates variable amounts of heat, depending on the particular parameters used. Therefore, the sonification module in some embodiments, is sequentially or simultaneously coupled with an environmental module that decreases the temperature of the blood or blood fraction. In certain embodiments, the temperature module is used to lower the temperature of the blood or blood fraction about 5° C. to about 25° C., about 5° C. to about 15° C., about 10° C. to about 25° C., about 5° C. to about 10° C., about 8° C. to about 12° C., or about 8° C. to about 10° C.

F. Toxin Removal Module

The extracorporeal system of the invention may include one or more toxin removal modules, such as a filtration module, a dialysis module, a chelation module, and/or an absorption or adsorption module, to remove both pathogenic endotoxins as well as potentially toxic drugs, drug components, or drug byproducts (FIGS. 10-13). In other embodiments, the extracorporeal system of the invention does not include a toxin removal module.

1. Filtration Module

In certain embodiments, the extracorporeal system includes one or more filtration modules. A filtration module may include conventional means for capturing pathogens and/or other toxins while permitting other blood components to pass through. The filter can be a mechanical filter such as a screen or membrane or it can include an affinity-based method of capture such as with antibody capture resins (e.g., monoclonal antibodies with magnetic nanoparticles). In certain embodiments, the filter is a polymyxin cartridge which removes bacterial endotoxins from the blood or blood fraction. Filtration and removal of intact bacteria not only decreases bacterial load, but also reduces or eliminates the production of endotoxins, which are potentially lethal.

Nevertheless, especially for modules including pharmaceutical and/or radiation modules, in one embodiment, the filtration module may include an endotoxin filter, such as a polymyxin cartridge (See FIG. 10).

In another embodiment, the filter can be a ceramic filter having an average pore size of about 0.1 to about 5 microns, about 0.3 to about 1.5 microns, or about 1 micron. In certain embodiments, the ceramic filter has an average pore size of about 0.05 to about 0.15 microns, and the filter can trap a virus. In certain other embodiments, the ceramic filter has an average pore size from about 1.5 to about 5 microns, and the filter can trap bacteria. In certain other embodiments, the ceramic filter has an average pore size from about 12 to about 50 microns, or larger, and the filter can trap parasites and fungi.

In another embodiment, the filtration module can utilize an electrical charge gradient to move the blood across the filter (i.e., electrodialysis). Gram positive bacteria have negative surface charges due to their carboxyl and phosphate capsular components. This allows them to migrate through the membrane towards a positive electrodialytic charge, and then be sequestered and eliminated from the circuit.

In one embodiment, whole blood, or one or more blood fractions, are passed through one or more filtration modules. In one embodiment, a plasma fraction is passed through a filtration module utilizing a ceramic filter. Additionally or alternatively, a red blood cell fraction can be diluted with normal saline then, as an alternative to centrifugation, be subjected to bacterial filtration by electrodialysis, through a membrane having an average pore size of about 0.1 to about 2 microns, about 0.2 to about 2 microns, about 0.3 to about 2 microns, about 0.1 to about 1.5 microns, about 0.2 to about 1.5 microns, or about 0.3 to about 1.5 microns.

2. Dialysis Module

In certain embodiments, the extracorporeal system includes one or more dialysis modules (FIG. 11). In certain embodiments of the present extracorporeal system, antimicrobial molecules (e.g., antibiotics) will be used in the treatment module that would have deleterious effects on a subject if the molecules were introduced into the subject. Therefore, prior to returning the blood or blood fraction to the subject, the blood or blood fraction is subjected to dialysis in order to reduce the concentration of the antimicrobial molecules. Whether a particular antimicrobial molecule may be removed by dialysis is dependent at least in part on molecular weight, charge, and albumin binding. In certain embodiments, the dialysis is conducted for about 2 to about 6 hours, about 3 to about 5, or about 4 to about 5 hours. In certain embodiments, the antimicrobial molecule concentration is reduced to about 5% to about 50% of its pre-dialysis concentration, and the remaining molecules may be cleared by the subject's kidneys. Examples of antimicrobial molecules that may effectively be dialyzed from the blood or blood fraction are shown in Table 3 (extracted from http://www.clinicaldruguse.com/dialysis-Drugs.php accessed on Dec. 28, 2011).

TABLE 3

| Drugs<br>Antimicrobial Agents | Percent removed<br>By hemodialysis | Percent removed<br>By CAPD |
|---|---|---|
| Aminoglycosides | | |
| Aminoglycosides | 50% | 20-50% |
| Spectinomycin | 50% | — |
| Carbapenems | | |
| Biapenem | 90% | — |
| Imipenem | 80-90% | Negligible |
| Meropenem | 50-70% | — |
| Cephalosporins | | |
| Cefaclor | 33% | — |
| Cefadroxil | 50% | — |
| Cefamandole | 50% | Negligible (5%) |

TABLE 3-continued

| Drugs Antimicrobial Agents | Percent removed By hemodialysis | Percent removed By CAPD |
|---|---|---|
| Cefazolin | 50% | 20% |
| Cefipime | 40-70% | 26% |
| Cefmenoxime | 16-51% | Negligible (<10%) |
| Cefmetazole | 60% | — |
| Cefodizime | 50% | Negligible (15%) |
| Ceforanide | 20-50% | Negligible |
| Cefotaxime | 60% | Negligible (5%) |
| Defotiam | 30-40% | — |
| Cefoxitin | 50% | Negligible |
| Cefpirome | 32-48% | Negligible (12%) |
| Cefpodoxime | 50% | — |
| Cefprozil | 55% | — |
| Cefroxadine | 50% | — |
| Cefsulodin | 60% | — |
| Ceftazidime | 50% | Negligible |
| Ceftibuten | 39% | — |
| Ceftizoxime | 50% | Negligible (16%) |
| Ceftriaxone | 40% | Negligible (4.5%) |
| Cefuroxime | — | 20% |
| Cephacetrile | 50% | — |
| Cephalexin | 50-75% | 30% |
| Cephalothin | 50% | — |
| Cephapirin | 20% | — |
| Monobactams | | |
| Aztreoman | 40% | Negligible |
| Carumonam | 51% | — |
| Moxalactam | 30-50% | Negligible (15-20%) |
| Nitroimidazoles | | |
| Metronidazole | 45% | Negligible (10%) |
| Ornidazole | 42% | Negligible (6%) |
| Tinidazole | 40% | — |
| Oxaxolindiones | | |
| Linezolid | 33% | — |
| Penicillins | | |
| Amdinocillin | 32-70% | Negligible (<4%) |
| Amoxicillin | 30% | — |
| Ampicillin | 40% | — |
| Azlocillin | 30-45% | — |
| Carbenicillin | 50% | — |
| Mezlocillin | 20-25% | 24% |
| Penicillin | 50% | — |
| Piperacillin | 30-50% | — |
| Temocillin | 50% | Negligible (6%) |
| Ticarcillin | 50% | Negligible |
| Sulfonamides | | |
| Sulfamethoxazole | 50% | Negligible (8%) |
| Trimethoprim | 50% | Negligible (7%) |
| Antifungals | | |
| Fluconazole | 40% | Negligible (18%) |
| Flucytosine | 50% | — |
| Antituberculous Agents | | |
| Para-aminosalicylic Acid | 50% | — |
| Isoniazid | 75% | — |
| Antiviral Agents | | |
| Abacavir | 24% | — |
| Acyclovir | 60% | Negligible (<10%) |
| Cidofovir | 50% | Negligible |
| Didanosine | 20-67% | Negligible |
| Vidarabine | 50% | — |

3. Chelation Module

In certain embodiments, the extracorporeal system includes one or more chelation modules (FIG. 12). In certain embodiments of the present extracorporeal system, heavy metal legacy antimicrobial compounds will be used in the treatment module that would have deleterious effects on a subject if the compounds were introduced into the subject. Legacy antimicrobial substances include heavy metal and transitional metal agents such as arsenic, mercury, antimony and lead that were used in various forms. These compounds possessed very significant antimicrobial effectiveness, but were limited by their systemic toxicity in humans. Therefore, prior to returning the blood or blood fraction to the subject, the blood or blood fraction is contacted with a chelating agent in order to inactivate the antimicrobial molecules.

Chelating agents are chemical compounds that are capable of tightly binding the ions of such metallic antimicrobial preparations and inactivating their toxic effects. The inactivated chelated metal ion complexes are water soluble and are able to be eliminated from the body via the patient's kidneys. The first practical chelating agent for heavy metal poisoning was developed during world War I to combat poisoning produced by weaponized arsenical gas preparations, and was known as BAL, or British Anti-Lewisite. The disclosed extracorporeal systems will allow for further practical research and development of new forms of metallic antimicrobial agents, in order to provide increased effectiveness against resistant microbial pathogens.

Suitable chelation agents are any that are known to one of ordinary skill in the art, and many are currently commercially available for use in the treatment of poison victims, such as BAL (for use with, e.g., lead, mercury, arsenic), dimercaptosuccinic acid (DMSA) (for use with, e.g., lead, mercury, cadmium, arsenic), desferal, 2,3-dimercapto-1-propanesulfonic acid (DMPS) (for use with, e.g., severe acute arsenic and mercury poisoning), pencillamine (for use with, e.g., copper, gold, lead), ethylenediaminetetraacetic acid (EDTA) (for use with, e.g., lead), deferoxamine (for use with, e.g., iron), deferasirox (for use with, e.g., iron), thiobendazole (for use with, e.g., antimony), and alpha lipoic acid (ALA).

4. Absorption Module

In certain embodiments, the extracorporeal system includes one or more absorption modules (FIG. 13). Adsorbent filters, cartridges, or columns may be used to physically bond to and retain toxins on their surface. Absorbent filters, cartridges, or columns may be used to chemically integrate the toxin molecule into the structure of the filter, cartridge, or column. Any adsorbent or absorbent filter material known to one of skill in the art may be used. In certain embodiments, the adsorbent or absorbent filter, cartridge, or column comprises a material that is selected from a group that includes, but is not limited to activated charcoal, soda lime, and polymixin. In certain embodiments, the adsorption or absorption filter, cartridge, or column is used to remove the toxin or other unwanted non-dialyzable substances from the fluid, and the filter, cartridge, or column is discarded. In one embodiment, the absorbent material may be soda lime, and it may be used to remove carbon dioxide from the fluid. In another embodiment, the adsorbent material is polymixin, and it may be used to adsorb bacterial endotoxins to the polymixin coated fibers, which are then discarded.

G. Blood return

Blood return, like blood removal described above, can be accomplished by any conventional means, e.g., catheter or port, known in the art. The blood return port and the blood removal port can enter the patient at the same approximate location (e.g., the same arm as depicted in FIG. 1), or the blood removal port and blood return may have entirely independent entry points.

II. Research Tools

The extracorporeal system and methods of the invention may be used for research purposes in which case, the subject may be a small mammal laboratory animal such as a mouse, rat, or rabbit. In other embodiments, the subject may be replaced by a non-living blood source, such as a blood reservoir (containing e.g., fresh animal blood), to create a free-standing, closed circuit.

The extracorporeal systems and methods of the invention may be used to develop new drugs or new classes of drugs, screen drugs to assess the extracorporeal efficacy under various conditions. In particular, the invention may be used to assess and discover drugs that are effective in conditions of low glucose, anaerobic, or other fermentative conditions.

The invention can also be used for culturing pathogens. Culturing pathogens in this device allows for continuous control of various environmental factors as well as the added advantage of mimicked circulation and other in vivo effects, such as the creation of, and treatment for, biofilms.

Without further elaboration, it is believed that one skilled in the art using the preceding description can utilize the invention to the fullest extent.

The embodiments described above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in biology or in the relevant fields are intended to be within the scope of the appended claims.

The disclosures of all references and publications cited above are expressly incorporated by reference in their entireties to the same extent as if each were incorporated by reference individually.

What is claimed is:

1. An extracorporeal method for treating a blood-borne disease comprising the steps of:
   a) removing blood from a subject;
   b) contacting the blood with an anticoagulant;
   c) optionally separating the blood into two or more blood fractions;
   d) modifying the environment of the blood or a blood fraction by deoxygenating the blood or blood fraction;
   e) treating the blood or blood fraction with a first pharmaceutical agent that is effective in anaerobic conditions;
   f) modifying the environment of the blood or blood fraction, wherein this second step of modifying the environment does not comprise deoxygenating the blood or blood fraction;
   g) treating the blood or blood fraction with hydrostatic pressure, a pulsed electrical field, a second pharmaceutical agent, centrifugation, microwave, radiation, sonification, or a combination thereof; and
   h) returning at least a portion of the blood or blood fraction to the subject.

2. The method of claim 1, wherein the anticoagulant is heparin or sodium citrate.

3. The method of claim 1, wherein the blood is separated into a red blood cell fraction, a buffy coat fraction, a platelet fraction, a plasma fraction, or a combination thereof.

4. The method of claim 3, wherein some or all of the buffy coat portion is not returned to the subject.

5. The method of claim 1, wherein the second step of modifying the environment of the blood or a blood fraction comprises at least one of modifying the pH, modifying the temperature, increasing the oxygenation, modifying the available nutrients, modifying the carbon dioxide, modifying the osmolality, or a combination thereof.

6. The method of claim 5, wherein the second step of modifying the environment comprises lowering the pH, and wherein the second treating step comprises treating the blood or blood fraction with a pharmaceutical agent is that is acidic.

7. The method of claim 6, wherein the step of lowering the pH comprises contacting the blood or blood fraction with carbonic acid, ammonium chloride, citric acid, hydrochloric acid, lactic acid, acetic acid, pyruvic acid, or a combination thereof.

8. The method of claim 5, wherein the second step of modifying the environment comprises increasing the pH of the blood or blood fraction, and wherein the second treating step comprises treating the blood or blood fraction with a pharmaceutical agent that is basic.

9. The method of claim 8, wherein the step of increasing the pH comprises contacting the blood with bicarbonate.

10. The method of claim 5, wherein the second step of modifying the environment comprises reducing the blood or blood fraction temperature to about 30° C. to about 36° C.

11. The method of claim 5, wherein the second step of modifying the environment comprises increasing the blood or blood fraction temperature to about 37° C. to about 42° C.

12. The method of claim 5, wherein the second step of modifying the environment comprises oxygenating the blood or blood fraction.

13. The method of claim 5, wherein the second step of modifying the environment comprises adding glucose to the blood or blood fraction.

14. The method of claim 5, wherein the second step of modifying the environment comprises reducing glucose in the blood or blood fraction.

15. The method of claim 5, wherein the second step of modifying the environment comprises increasing the carbon dioxide in the blood or blood fraction.

16. The method of claim 5, wherein the second step of modifying the environment comprises reducing the temperature of the blood or blood fraction, and wherein the second treating step comprises treating the blood or blood fraction with hydrostatic pressure.

17. The method of claim 1, wherein the first pharmaceutical agent is metronidazole, clindamycin, or combinations thereof.

18. The method of claim 1, wherein the second step of modifying the environment of the treated blood or blood fraction comprises oxygenating the treated blood or blood fraction; and wherein the second treating step comprises administering to the blood or blood fraction a second pharmaceutical agent effective in aerobic conditions.

19. The method of claim 18, wherein the second pharmaceutical agent is daptomycin, azithromycin, silver, or combinations thereof.

20. The method of claim 1, wherein the second treating step comprises treating the blood or blood fraction with hydrostatic pressure at a pressure range from about 50 MPa to about 1,000 MPa.

21. The method of claim 1, wherein the second treating step comprises treating the blood or blood fraction with a pulsed electrical field and a pharmaceutical agent.

22. The method of claim 1, wherein the second step of modifying the environment comprises reducing the blood or blood fraction temperature, and wherein the second treating step comprises treating the blood or blood fraction with a pulsed electrical field and a pharmaceutical agent.

23. The method of claim 1, wherein the second step of modifying the environment comprises reducing the blood or blood fraction temperature, and wherein the second treating step comprises treating the blood or blood fraction with microwaves.

24. The method of claim 1, wherein the second treating step comprises treating the blood or blood fraction solely by centrifugation.

25. The method of claim 1, further comprising a step of irradiating the blood or blood fraction after the treating steps.

26. The method of claim 25, wherein the step of irradiating the blood comprises exposing the blood or blood fraction to X-ray, UV, IR, visible, laser, radiofrequency energy, or a combination thereof.

27. The method of claim 25, wherein the step of irradiating the blood or blood fraction comprises exposing the blood or blood fraction to about 50 to about 75 gray units.

28. The method of claim 1, further comprising a step of removing toxins from the blood or blood fraction after the treating steps, wherein the step of removing toxins comprises filtering the blood or blood fraction, dialyzing the blood or blood fraction, chelating the blood or blood fraction, absorbing toxins from the blood or blood fraction, or a combination thereof.

29. The method of claim 28, wherein the filtering step comprises directing the blood through a filter having an average pore size of about 0.3 to about 1.5 microns.

30. The method of claim 28, wherein the filtering step comprises directing the blood through an antibody capture module.

31. The method of claim 30, wherein the antibody capture module comprises monoclonal antibodies with magnetic nanoparticles.

32. The method of claim 1, further comprising the step of:
   g) repeating step d), step e), or both step d) and step e) at least one time.

33. An extracorporeal system for use in the method of claim 1, comprising:
   a) a blood removal port;
   b) an anticoagulant module;
   c) a first module adapted to modify the environment of blood or a blood fraction by deoxygenating the blood or blood fraction;
   d) a first treatment module adapted to administer a first pharmaceutical agent;
   e) a second module adapted to modify the environment of the blood or blood fraction;
   f) a second treatment module adapted to administer hydrostatic pressure, a pulsed electrical field, a second pharmaceutical agent, microwave, centrifugation, radiation, sonification, or a combination thereof; and
   g) a blood return port.

34. The extracorporeal system of claim 33, wherein the second environmental module comprises at least one of a pH-modifying module, an oxygenation module, a temperature adjustment module, a carbon dioxide module, and an osmolality module.

35. The extracorporeal system of claim 34, wherein the second environmental module is a pH-modifying module, and wherein the second treatment module is adapted to administer a second pharmaceutical agent that is effective at a certain pH range.

36. The extracorporeal system of claim 34, wherein the second environmental module oxygenates the blood or blood fraction, and wherein the second treatment module is adapted to administer a second pharmaceutical agent that is effective in aerobic conditions.

37. The extracorporeal system of claim 33, wherein the second environmental module decreases the temperature of the blood or blood fraction, and wherein the second treatment module is adapted to administer hydrostatic pressure, a pulsed electrical field, or a combination thereof.

38. An extracorporeal system for use in the method of claim 1 for the treatment of MRSA in a subject, comprising:
   a) a blood removal port;
   b) an anticoagulant module;
   c) a module to separate the blood into a red blood cell fraction, a buffy coat fraction, and a plasma fraction;
   d) at least one module that is adapted to administer silver ions to the red blood cell fraction;
   e) at least one module that is adapted to administer a pharmaceutical agent that is effective in aerobic conditions;
   f) a module to decrease the oxygenation of the red blood cell fraction;
   g) at least one module that is adapted to administer a pharmaceutical agent that is effective in anaerobic conditions;
   h) a radiation module;
   i) a filtration module; and
   j) a blood return port.

39. A method for developing a new drug or treatment regimen in an extracorporeal system for the treatment of a subject, said method comprising the steps of:
   a) obtaining a blood sample that contains a known concentration of pathogens;
   b) optionally separating the blood sample into a red blood cell fraction, a buffy coat fraction, a plasma fraction, or a combination thereof;
   c) modifying the environment of at least a portion of the blood sample or a blood fraction by deoxygenating the blood or blood fraction;
   d) treating the blood or blood fraction with a first pharmaceutical agent that is effective in anaerobic conditions;
   e) modifying the environment of the blood or blood fraction, wherein this second step of modifying the environment does not comprise deoxygenating the blood or blood fraction;
   f) treating the blood sample or blood fraction with hydrostatic pressure, a pulsed electrical field, a second pharmaceutical agent, microwave, centrifugation, radiation, sonification, or a combination thereof; and
   g) determining the concentration of pathogens in the blood sample or blood fraction after the treating steps, wherein the treatment is successful for the pathogen if it eliminates or reduces the concentration of the pathogens in the blood sample or blood fraction when compared to the known concentration from step a).

40. A method for treatment of a blood sample or blood fraction prior to transfusion to a subject, said method comprising the steps of:
   a) obtaining a blood sample or blood fraction;
   b) optionally separating the blood sample or blood fraction into a red blood cell fraction, a buffy coat fraction, a plasma fraction, or a combination thereof;
   c) modifying the environment of at least a portion of the blood sample or the blood fraction by deoxygenating the blood or blood fraction;
   d) treating the blood or blood fraction with a first pharmaceutical agent that is effective in anaerobic conditions;
   e) modifying the environment of the blood or blood fraction, wherein this second step of modifying the environment does not comprise deoxygenating the blood or blood fraction;
   f) treating the blood sample or blood fraction with hydrostatic pressure, a pulsed electrical field, a second pharmaceutical agent, microwave, centrifugation, radiation, sonification, or a combination thereof; and g) determining the concentration of pathogens in the blood sample or blood fraction after the second treating step.

41. An extracorporeal method for treating a blood-borne disease comprising the steps of:

a) removing blood from a subject;
b) contacting the blood with an anticoagulant;
c) optionally separating the blood into two or more blood fractions;
d) deoxygenating the blood or blood fraction by passing the blood or blood fraction through a membrane exchanger to remove oxygen;
e) treating the blood or blood fraction with a first pharmaceutical agent that is effective in anaerobic conditions;
f) optionally modifying the environment of the blood or blood fraction, wherein this optional second step of modifying the environment does not comprise deoxygenating the blood or blood fraction;
g) optionally treating the blood or blood fraction with hydrostatic pressure, a pulsed electrical field, a second pharmaceutical agent, centrifugation, microwave, radiation, sonification, or a combination thereof; and
h) returning at least a portion of the blood or blood fraction to the subject.

42. The method of claim 41, wherein the anticoagulant is heparin or sodium citrate.

43. The method of claim 41, wherein the optional second step of modifying the environment of the blood or a blood fraction comprises at least one of modifying the pH, modifying the temperature, increasing the oxygenation, modifying the available nutrients, modifying the carbon dioxide, modifying the osmolality, or a combination thereof.

* * * * *